US012611105B2

(12) United States Patent
Gopinath et al.

(10) Patent No.: US 12,611,105 B2
(45) Date of Patent: Apr. 28, 2026

(54) ARTERIAL IMAGING AND ASSESSMENT SYSTEMS AND METHODS AND RELATED USER INTERFACE BASED-WORKFLOWS

(71) Applicant: LightLab Imaging, Inc., Westford, MA (US)

(72) Inventors: Ajay Gopinath, Bedford, MA (US); Mark Hoeveler, Eliot, ME (US)

(73) Assignee: LightLab Imaging, Inc., Westford, MA (US)

( * ) Notice: Subject to any disclaimer, the term of this patent is extended or adjusted under 35 U.S.C. 154(b) by 0 days.

(21) Appl. No.: 18/385,462

(22) Filed: Oct. 31, 2023

(65) Prior Publication Data

US 2024/0057870 A1 Feb. 22, 2024

Related U.S. Application Data

(63) Continuation of application No. 18/237,614, filed on Aug. 24, 2023, which is a continuation of application
(Continued)

(51) Int. Cl.
*G06F 3/048* (2013.01)
*A61B 5/00* (2006.01)
(Continued)

(52) U.S. Cl.
CPC ............ *A61B 5/0066* (2013.01); *A61B 34/10* (2016.02); *A61B 34/25* (2016.02); *G06F 3/0484* (2013.01);
(Continued)

(58) Field of Classification Search
CPC ....... A61B 5/0066; A61B 34/10; A61B 34/25; G06T 7/62; G06T 7/13; G06T 7/0012;
(Continued)

(56) References Cited

U.S. PATENT DOCUMENTS 7,860,283 B2 12/2010 Begelman et al.
8,167,805 B2 5/2012 Emery et al.
(Continued)

FOREIGN PATENT DOCUMENTS

CN 104224217 A 12/2014
JP 2008543511 A 12/2008
(Continued)

OTHER PUBLICATIONS

Partial International Search Report for Application No. PCT/US2020/ 023213 mailed Jul. 23, 2020, 4 pages.
(Continued)

*Primary Examiner* — David Phantana-angkool
(74) *Attorney, Agent, or Firm* — Lerner David LLP

(57) ABSTRACT

In part, the disclosure relates to method of displaying a representation of an artery. The method may include storing an intravascular image dataset in a memory device of a diagnostic imaging system, the intravascular image dataset generated in response to intravascular imaging of a segment of an artery; automatically detecting lumen boundary of the segment on a per frame basis; automatically detecting EEL and displaying a stent sizing workflow. In part, the disclosure also relates to automatically detecting one or more regions of calcium relative to lumen boundary of the segment; calculating an angular or circumferential measurement of detected calcium for one or more frames; calculating a calcium thickness of detected calcium for one or more frames; and displaying the calcium thickness and the angular or circumferential measurement of detected calcium for a first frame of the one or more frames.

19 Claims, 21 Drawing Sheets
(19 of 21 Drawing Sheet(s) Filed in Color)

Related U.S. Application Data

No. 16/821,877, filed on Mar. 17, 2020, now Pat. No. 11,819,309.

(60) Provisional application No. 62/819,595, filed on Mar. 17, 2019.

(51) Int. Cl.

| | |
|---|---|
| *A61B 34/00* | (2016.01) |
| *A61B 34/10* | (2016.01) |
| *G06F 3/0484* | (2022.01) |
| *G06T 7/00* | (2017.01) |
| *G06T 7/13* | (2017.01) |
| *G06T 7/62* | (2017.01) |
| *G06V 10/764* | (2022.01) |
| *G06V 10/82* | (2022.01) |
| *G16H 30/20* | (2018.01) |
| *G16H 30/40* | (2018.01) |
| *G16H 40/40* | (2018.01) |
| *G16H 40/63* | (2018.01) |
| *A61F 2/958* | (2013.01) |

(52) U.S. Cl.

CPC .............. *G06T 7/0012* (2013.01); *G06T 7/13* (2017.01); *G06T 7/62* (2017.01); *G06V 10/764* (2022.01); *G06V 10/82* (2022.01); *G16H 30/20* (2018.01); *G16H 30/40* (2018.01); *G16H 40/40* (2018.01); *G16H 40/63* (2018.01); *A61B 2034/107* (2016.02); *A61B 2034/108* (2016.02); *A61F 2/958* (2013.01); *G06T 2200/24* (2013.01); *G06T 2207/30052* (2013.01); *G06T 2207/30101* (2013.01); *G06V 2201/03* (2022.01)

(58) Field of Classification Search

CPC ........ G16H 30/20; G16H 30/40; G16H 40/40; G16H 40/63; G06V 10/82; G06V 10/764; G06F 3/0484

See application file for complete search history.

(56) References Cited

U.S. PATENT DOCUMENTS

| | | | |
|---|---|---|---|
| 9,138,147 B2 | 9/2015 | Schmitt et al. | |
| 9,940,723 B2 | 4/2018 | Gopinath et al. | |
| 10,631,754 B2 * | 4/2020 | Gopinath | A61B 5/725 |
| 11,064,873 B2 | 7/2021 | Petroff et al. | |
| 11,278,206 B2 | 3/2022 | Petroff et al. | |
| 11,571,129 B2 * | 2/2023 | Kunio | A61B 8/12 |
| 11,684,242 B2 | 6/2023 | Petroff et al. | |
| 11,883,107 B2 | 1/2024 | Gopinath | |
| 11,887,734 B2 * | 1/2024 | Buckler | G16H 50/20 |
| 11,923,067 B2 * | 3/2024 | Schmitt | A61B 5/0066 |
| 12,036,074 B2 | 7/2024 | Booker et al. | |
| 12,239,412 B2 | 3/2025 | Petroff et al. | |
| 2007/0167710 A1 | 7/2007 | Unal et al. | |
| 2011/0071404 A1 | 3/2011 | Schmitt et al. | |
| 2012/0075638 A1 | 3/2012 | Rollins et al. | |
| 2012/0253186 A1 | 10/2012 | Simpson et al. | |
| 2012/0283569 A1 | 11/2012 | Ciompi et al. | |
| 2013/0030295 A1 | 1/2013 | Huennekens et al. | |
| 2013/0072805 A1 | 3/2013 | Schmitt et al. | |
| 2014/0100442 A1 | 4/2014 | Begin et al. | |
| 2014/0270430 A1 | 9/2014 | Nair | |
| 2014/0378850 A1 | 12/2014 | Plakas et al. | |
| 2015/0297373 A1 * | 10/2015 | Schmitt | A61F 2/86 623/1.16 |
| 2016/0135832 A1 | 5/2016 | Simpson et al. | |
| 2016/0171711 A1 | 6/2016 | Gopinath et al. | |
| 2016/0335763 A1 * | 11/2016 | Ambwani | G06V 10/507 |
| 2016/0335766 A1 * | 11/2016 | Ambwani | G06T 7/11 |
| 2017/0143296 A1 | 5/2017 | Peterson et al. | |
| 2017/0325712 A1 * | 11/2017 | Gopinath | G06T 7/73 |
| 2018/0085170 A1 | 3/2018 | Gopinath | |
| 2019/0099080 A1 | 4/2019 | Kunio et al. | |
| 2019/0365480 A1 * | 12/2019 | Gopinath | A61B 5/4851 |
| 2020/0129147 A1 * | 4/2020 | Nair | A61B 8/469 |
| 2020/0202564 A1 * | 6/2020 | Kunio | G06T 7/13 |
| 2020/0226422 A1 * | 7/2020 | Li | G06N 3/04 |
| 2020/0294659 A1 * | 9/2020 | Gopinath | A61B 34/10 |
| 2021/0042927 A1 * | 2/2021 | Amis | G16H 30/40 |
| 2022/0117551 A1 * | 4/2022 | Gopinath | A61B 5/0066 |
| 2023/0005139 A1 * | 1/2023 | Blaber | G06T 11/008 |
| 2024/0032894 A1 * | 2/2024 | Peterson | A61B 5/0084 |
| 2024/0057870 A1 * | 2/2024 | Gopinath | G16H 30/20 |
| 2024/0086025 A1 * | 3/2024 | Imura | A61B 8/469 |
| 2024/0268694 A1 * | 8/2024 | Robinson | A61B 5/02007 |
| 2024/0316327 A1 | 9/2024 | Densley et al. | |
| 2024/0346670 A1 * | 10/2024 | Li | A61B 8/463 |
| 2024/0382180 A1 * | 11/2024 | Shang | G06T 7/33 |
| 2025/0117952 A1 * | 4/2025 | Akakin | A61B 8/5207 |
| 2025/0117953 A1 * | 4/2025 | Li | G06T 7/337 |
| 2025/0117962 A1 * | 4/2025 | Li | G06T 7/62 |
| 2025/0166187 A1 | 5/2025 | Golden et al. | |
| 2025/0217985 A1 * | 7/2025 | Bruch El | G16H 50/20 |

FOREIGN PATENT DOCUMENTS

| | | |
|---|---|---|
| JP | 2013505782 A | 2/2013 |
| JP | 2013-154192 A | 8/2013 |
| JP | 2016-508750 A | 3/2016 |
| JP | 2016-526470 A | 9/2016 |
| JP | 2017-537768 A | 12/2017 |
| WO | 2014092755 A1 | 6/2014 |
| WO | 2017130927 A1 | 8/2017 |

OTHER PUBLICATIONS

Ali, et al., "Intracoronary Optical Coherence Tomography 2018 Current Status and Future Directions," JACC: Cardiovascular Interventions, Elsevier, Amsterdam, NL, Dec. 18, 2017, pp. 2473-2487, vol. 10, No. 24, XP085314412.

Maehara, et al., "IVUS-Guided Versus OCT-Guided Coronary Stent Implantation A Critical Appraisal," JACC: Cardiovascular Imaging, Dec. 1, 2017, pp. 1487-1503, vol. 10, No. 12, XP085302795.

Shimamura, et al., "Optical Coherence Tomography for Online Guidance of Complex Coronary Interventions," Circulation Journal, Sep. 9, 2016, pp. 2063-2072, vol. 80, No. 10, XP055708068.

International Search Report including Written Opinion for Application No. PCT/US2020/023213, mailed Oct. 29, 2020, pp. 1-22.

Athanasiou et al., Methodology for fully automated segmentation and plaque characterization in intracoronary optical coherence tomography images, Journal of Biomedical Optics, SPIE, Feb. 2014, p. 26009 (13 pages), vol. 19, No. 2, XP060047308, ISSN: 1083-3668, DOI: 10.1117/1.JB0.19.2.026009.

Gao et al., Automated Detection Framework of the Calcified Plaque with Acoustic Shadowing in IVUS Images, Plos One, Nov. 2014, p. e109997 (18 pages), vol. 9, No. 11, XP055215949, DOI:10.1371/journal.pone.0109997.

Athanasiou et al., Fully automated calcium detection using optical coherence tomography, Engineering in Medicine and Biology Society (EMBC), 35th Annual International Conference of the IEEE, Jul. 2013, pp. 1430-1433, XP032489515, ISSN:1557-170X, DOI:10.1109/EMBC.2013.6609779.

Second Chinese Office Action issued in Appln. No. 202080022148.9 mailed Jan. 25, 2024 (8 pages).

Japanese Office Action issued in Appln. No. 2021-556302 mailed Mar. 1, 2024 (5 pages).

Japanese Search Report issued in Appln. No. 2021-556302 mailed Dec. 26, 2023 (12 pages).

Bonnema, Garret T et al. "An automatic algorithm for detecting stent endothelialization from volumetric optical coherence tomography datasets." Physics in medicine and biology vol. 53,12 (Jun. 2008): 3083-98. doi: 10.1088/0031-9155/53/12/001.

Communication pursuant to Article 94(3) EPC for Application No. 20719801.1 dated Jun. 28, 24. 4 pgs.

(56)           References Cited

OTHER PUBLICATIONS

Porto Italo, et al: "Long-term Morphofunctional Remodeling of Internal Thoracic Artery Grafts : A Frequency-Domain Optical Coherence Tomography Study", [Circulation I Cardiovascular interventions] Circulation : journal of the American Heart Association, vol. 6, No. 3, May 28, 2013 (May 28, 2013), pp. 269-276, XP93178445, US ISSN: 1941-7640, DOI: 10.1161/CIRCINTERVENTIONS.113. 000200.
Volcano Corporation, "VH IVUS The Gold Standard for Complete Lesion Assessment", Aug. 2013. 4 pgs.
Volcano Corporation, "The Volcano s5 Imaging System", Jan. 2013. 2 pgs.
Chinese Office Action issued in Appln. No. 202080022148.9 mailed Jul. 4, 2024 (6 pages).
Notice of Allowance for JP 2021-556302 mailed Sep. 3, 2024, 2 pages. (with English translation).

Nishioka T et al: "Clinical validation of intravascular ultrasound imaging for assessment of coronary stenosis severity: Comparison with stress myocardial perfusion imaging", Journal of the American College of Cardiology, vol. 33, No. 7, Jun. 1, 1999 (Jun. 1, 1999), pp. 1870-1878, XP093279136, Amsterdam, NL, ISSN: 0735-1097, DOI: 10.1016/S0735-1097(99)00100-X.
Communication pursuant to Article 94(3) EPC issued in Appln. No. 20719801.1 mailed May 27, 2025. (5 pages).
Japanese Office Action issued in Appln. No. 2024-174357 mailed Jun. 3, 2025 (8 pages).
Ali, Z., et al., "Optical coherence tomography compared with intravascular ultrasound and with angiography to guide coronary stent implantation (Ilumien III: Optimize PCI): a randomised controlled trial", Lancet, Oct. 30, 2016, Elsevier, vol. 388, Issue 10060, pp. 2618-2628 doi: 10.1016/S0140-6736(16)31922-5. 12 pgs.
Japanese Office Action issued in Appln. No. 2024-174357 dated Nov. 14, 2025. 3 pgs.

* cited by examiner

ARTERIAL IMAGING AND ASSESSMENT SYSTEMS AND METHODS AND RELATED USER INTERFACE BASED-WORKFLOWS

CROSS REFERENCE TO RELATED APPLICATIONS

This application is a continuation of U.S. patent application Ser. No. 18/237,614, filed Aug. 24, 2023, which is a continuation of U.S. patent application Ser. No. 16/821,877, filed Mar. 17, 2020 which claims priority to and the benefit of U.S. Provisional Patent Application No. 62/819,595 filed on Mar. 17, 2019, the entire disclosures of which are incorporated by reference therein.

BACKGROUND

Interventional cardiologists incorporate a variety of diagnostic tools during catheterization procedures in order to plan, guide, and assess therapies. Fluoroscopy is generally used to perform angiographic imaging of blood vessels. In turn, such blood vessel imaging is used by physicians to diagnose, locate and treat blood vessel disease during interventions such as bypass surgery or stent placement. Intravascular imaging technologies such as optical coherence tomography (OCT) are also valuable tools that can be used in lieu of or in combination with fluoroscopy to obtain high-resolution data regarding the condition of the blood vessels for a given subject.

Intravascular optical coherence tomography is a catheter-based imaging modality that uses light to peer into coronary artery walls and generate images thereof for study. Utilizing coherent light, interferometry, and micro-optics, OCT can provide video-rate in-vivo tomography within a diseased vessel with micrometer level resolution. Viewing subsurface structures with high resolution using fiber-optic probes makes OCT especially useful for minimally invasive imaging of internal tissues and organs. The level of detail made possible with OCT allows a user to diagnose as well as monitor the progression of coronary artery disease. Various other noninvasive imaging modalities may also be used in conjunction with OCT or separately to assess stenosis, Calcium, and other features or regions of interest.

Calcium plaques in blood vessels are a major cause of heart disease. Calcium deposition results in a narrowing of blood vessel diameter and also stiffens the blood vessel wall, which significantly reduces blood vessel performance. Calcium plaques therefore are one of the major targets of cardiovascular intervention.

Imaging of portions of arteries provides a useful diagnostic tool for doctors and others. For example, imaging of coronary arteries by intravascular may reveal the location of a narrowing or stenosis. This information helps cardiologists to choose between an invasive coronary bypass surgery and a less invasive catheter-based procedure such as angioplasty or stent delivery. Although a popular option, stent delivery has its own associated risks.

A stent is a tube-like structure that often is formed from a mesh. It can be inserted into a vessel and expanded to counteract a stenotic condition that constricts blood flow. Stents typically are made of a metal or a polymer scaffold. They can be deployed to the site of a stenosis via a catheter. During a cardiovascular procedure, a stent can be delivered to the stenotic site through a catheter via a guide wire, and expanded using a balloon. Typically, the stent is expanded using a preset pressure to enlarge the lumen of a stenosed vessel.

There are several factors that influence the patient outcome when deploying stents. In some procedures, the stent should be expanded to a diameter that corresponds to the diameter of adjacent healthy vessel segments. Stent overexpansion may cause extensive damage to the vessel, making it prone to dissection, disarticulation, and intra-mural hemorrhage. Stent under expansion may inadequately expand the vessel. If the portions of the stent fail to contact the vessel wall, the risk of thrombosis may increase. An under expanded stent may fail to restore normal flow. Clearly, after a stent is installed, stent over and under expansion of the stent can result in various problems.

There are other challenges associated with stent placements and related procedures. Visualizing a stent deployment relative to the wall of a blood vessel using an angiography system is challenging to undertake by inspection. All of the imaging modalities and tools available to clinicians can provide useful information, but care is necessary so as to not provide too much information to a clinician when diagnosing or operating in the cath law. Establishing workflows that use imaging modalities and other diagnostic tools in a balanced and forward thinking manner is an ongoing challenge.

Further, reviewing images and operating various screens and systems in a cath lab has various competing time constraints. Assessing a stenosis, planning for stent deployment, and otherwise exploring and understanding the landscape of a given coronary artery is no easy task. Tools and workflows and detection system and associated methods for planning, diagnosis, treatment, and checking are all challenging problems for which practical solutions are of great interest when it comes to increasing successfully procedures and a better understanding of the state of a given subjects cardiac system.

The present disclosure addresses these challenges and others.

SUMMARY

In one aspect, the disclosure relates to a method of displaying a representation of an artery. The method includes detecting an EEL-based metric on a per frame basis, using one or more processors, wherein a frame comprises a group of scan lines of the plurality of scan lines, computing, using the one or more processors, an EEL diameter or other EEL-based metric, detecting using the one or more processors, calcium at positions along a segment of the artery, and displaying a user interface on a display, the user interface comprising a first panel, wherein the display is in electrical communication with the intravascular imaging system. The method also includes where the first panel shows longitudinal view of a representation of a vessel that depicts a first indicia corresponding to one or more EEL-based metrics or an EEL diameter.

In one embodiment, the method further comprises displaying a second indicia corresponding to one or more regions of artery in which calcium has been detected. In one embodiment, the method further comprises displaying one or more of a lumen boundary, a minimum lumen area, or a measure of angular range of detected calcium relative to the user interface to guide stent planning or stenosis assessment. In one embodiment, the method further comprises displaying an indicia corresponding to a stent over a range of frames in response to detecting stent struts and displaying one or both of stent expansion metric and stent malapposition. In one embodiment, the method includes where detecting the lumen boundary comprises identifying a region as lumen boundary tissue on each scan line. In one embodiment, the method further includes determining a thickness value for one or more instances of detected calcium and displaying same to end user.

In one embodiment, the method also includes displaying a second panel in the user interface, the second panel comprising another view of the arterial representation. In one embodiment, the method also includes displaying a second panel in the user interface, the second panel comprising a first cross-sectional view of a position along the longitudinal section. In one embodiment, the method also includes displaying a percent diameter stenosis in the user interface.

In one embodiment, the method also includes displaying a proximal reference and a distal reference in the user interface. In one embodiment, the method also includes displaying a diameter value for the proximal reference and a diameter value for the distal reference. In one embodiment, the method also includes displaying a minimum lumen area for a subset of the longitudinal section between the proximal reference and the distal reference, wherein the minimum lumen area is determined on a per frame basis using a group of frames in the subset of the longitudinal section and the scan lines of the group of frames. In one embodiment, the method also includes superimposing a stent on the first longitudinal view. In one embodiment, the method also includes displaying an angular or circumferential measurement of detected calcium at one or more positions along the artery.

In one embodiment, the method includes identifying or detecting one or more regions or features of interest in image data obtained with regard to a section or segment of an artery. The regions or features of interest include one or more or all of the following calcium such as a calcified plaque or other arterial calcium deposit; lumen, arterial wall, lumen, lumen boundary, EEL, intima, media, sidebranches, stent struts, a tissue type, and other arterial features. In one embodiment, the image data comprises scan lines obtained using an intravascular/diagnostic system such OCT, IVUS, OFDI, and others. The image data may also include frames generated using intravascular imaging probes or other imaging modalities.

In one embodiment, the method includes displaying one or more representations of the section or segment of the artery in a graphical user interface. Various graphical user interfaces can be simultaneously displayed to a user that includes one or more of the regions and features of interest. The one or more regions or features of interest are detected automatically in one embodiment. In one embodiment, the representation of the segment of the artery is a two dimensional cross-sectional view of the artery, a two-dimensional longitudinal view of the segment of the artery or combinations of the foregoing which are displayed simultaneously with various of the features or regions of interest identified using an indicia, overlay, or other visible elements in the graphically user interface. The graphical user interfaces are arranged or grouped in a sequence of steps and informational presentation as workflows to guide an end user working with a subject in a cath lab or another environment. In one embodiment, the feature or region of interest is selected from the group includes intima, media, adventitia, lumen, EEL, IEL plaque, calcium, calcium plaques.

One or more arc lengths of a region of interest may be displayed such as in the instance of detected calcium. In one embodiment, discontinuous regions of calcium detections are combined such that one angular measurement of an overall angular measure of calcium is shown. Various indicia and graphic elements may be used which may include color, shapes, and other graphical elements or overlays. In various embodiment, the graphical user interfaces generated in conjunction with the operation and control of an imaging/diagnostic system is operable to include a set of graphical user interfaces organized in groups corresponding to a computer directed or computer-supported morphology workflow, a computer directed or computer-supported stent sizing/sizing workflow, a computer directed or computer-supported stent deployment/deployment workflow, a computer directed or computer-supported review/comparison workflow, combination thereof, and other workflows as disclosed herein. In some embodiments, the workflows are generated and displayed using graphical user interfaces that include one or more panels, automatically detected features and regions of interest identified using one or more indicia. The various workflow include representations of two-dimensional and/or three-dimensional views of artery such as cross-sectional views and longitudinal views showing lumen and calcium arc and EEL detections relative thereto.

In one aspect, the disclosure relates to a method of displaying a representation of an artery. The method includes storing an intravascular image data set in a memory device of a diagnostic imaging system, the intravascular image data set generated in response to intravascular imaging of a segment of an artery. The method also includes automatically detecting lumen boundary of the segment on a per frame basis. The method also includes automatically detecting external elastic lamina (EEL) of the segment on a per frame basis. The method also includes displaying a workflow operable for stent sizing comprising a graphical user interface, where the graphical user interface comprising a first representation of the artery at a first frame; and a second representation of the artery at a second frame, wherein a first EEL thickness and a first lumen thickness are displayed relative to the first representation, wherein a second EEL thickness and a second lumen thickness are displayed relative to the second representation.

In one embodiment, the method further comprises where the detected lumen boundary and detected EEL are identified relative to each respective representation using one or more indicia. In one embodiment, the method further comprises where the graphical user interface comprising a third representation of the artery at a third frame, wherein a third EEL thickness and a third lumen thickness are displayed relative to the third representation, wherein third frame may be selected and changed by a user through the graphical user interface. In one embodiment, the method further comprises where the third frame is selected from frames in between the first frame and the second frame. In one embodiment, the method further comprises where the graphical user interface further comprises a longitudinal representation of the artery that displays the first frame and the second frame relative thereto. In one embodiment, the method further comprises where the longitudinal representation comprises a lumen region, wherein lumen region is symmetric relative to longitudinal axis of the representation.

In one embodiment, the method further comprises where the graphical user interface further comprises a longitudinal representation of the artery that displays the detected EEL for a plurality of frames using one or more indicia. In one embodiment, the method further comprises where the first frame is a proximal reference frame and the second frame is a distal reference frame. In one embodiment, the method further comprises where a first portion of a representation of the proximal reference frame is identified with a first indicia and wherein a second portion of a representation of the distal reference frame is identified with a second indicia. In one embodiment, the method further comprises where the graphical user interface further comprises a longitudinal representation of the segment and displays a portion of first axis identified with the first indicia relative to the longitudinal representation. In one embodiment, the method further comprises where the graphical user interface comprises a third representation of the artery at a third frame and displays the portion of the first axis identified with the first indicia relative to the third representation.

In one embodiment, the method further comprises where the indicia is selected from the group of a color, a dotted line, hatching, graphical elements and overlays. In one embodiment, the method further comprises detecting calcium at positions along the segment and displaying an angular measure of total calcium relative for one or more frames in the graphical user interface. In one embodiment, the method further comprises receiving inputs from a user to select stent landing zones relative to a longitudinal representation of the segment. In one embodiment, the method further comprises displaying calculated stent length in response to user selected landing zones and displaying a minimum lumen diameter (MLD) relative to the longitudinal representation. In one embodiment, the method further comprises displaying option to select a stent deployment workflow after workflow operable for stent sizing. In one embodiment, the method further comprises option to select a review workflow after stent deployment, wherein the review workflow comprises a representation of a stented artery and one or more indicators of stent expansion percentage and stent malapposition.

In a second aspect, the disclosure relates to a method of displaying an artery. The method includes storing an intravascular image data set in a memory device of a diagnostic imaging system, the intravascular image data set generated in response to intravascular imaging of a segment of an artery. The method also includes automatically detecting one or more regions of calcium relative to lumen boundary of the segment on a per frame basis. The method also includes calculating an angular or circumferential measurement of detected calcium for one or more frames. The method also includes calculating a calcium thickness of detected calcium for one or more frames. The method also includes generating a first representation of the artery at one or more frames. The method also includes displaying the calcium thickness and the angular or circumferential measurement of detected calcium for a first frame of the one or more fames. The method also includes displaying an indicia indicative of the angular or circumferential measurement relative to the first representation of the artery.

In one embodiment, the method further comprises generating a second representation of the artery, the second representation comprising a longitudinal representation of the artery; and displaying an indicia corresponding to detection of calcium on a per frame basis. In one embodiment, the method further comprise automatically detecting external elastic lamina (EEL) of the segment on a per frame basis and displaying an indicia corresponding to EEL on a per frame basis of the longitudinal representation.

The various workflows and underlying graphical user interfaces organized relative to morphology, pre-treatment, stent planning/stent sizing, stent deployment, and review of procedure using multiple sets of image data may include and display one or more and combinations of scores, measurements, totally angle, maximum thickness, EEL, lumen, sidebranch, calcium, calcium angle, frame, proximal end or frame of artery segment being imaged and displayed, distal end or frame of artery segment being imaged and displayed, selected frame, flags, book marks, proximal reference, distal reference, lumen boundary, angiography images and co-registration indicia displayed relative to image data obtained within or relative to artery, a first pullback, a second pullback, an nth pullback, diameter of EEL, measurement of EEL, EEL metric, score generated using calcium angle and EEL thickness, stent expansion percentage, stent apposition, stent malapposition, total calcium angle, minimum lumen area, minimum lumen diameter, lumen thickness, stenosis, stent expansion threshold, stent apposition threshold, calcium threshold, 0 degree to about 360 degrees of calcium, circumferential calcium arc, and others.

In part, the disclosure relates to a system for identifying regions of interest in a blood vessel, such as an artery the system includes: a processor in communication with a memory, the memory containing instructions that when executed cause the processor to: obtain image data of the blood vessel; detect or segment image data, such as scan lines, frames, pixels, and combinations thereof identify feature of region of interest, display blood vessel representation with one or more graphic user interfaces organized and displayed as part of a diagnosis, treatment, In one embodiment, the image data is a plurality of scan lines. In one embodiment, the image data is a polar image.

In part, one embodiment of the disclosure relates to an intravascular data collection system and one or more software-based graphic user interfaces and software modules to perform one or more detection and display processes as described herein. In one embodiment, intravascular data is collected while angiography data is simultaneously collected. In this way, one or more representations of artery, such as cross-sectional and/or longitudinal views may be co-registered with angiography data. In one embodiment, the disclosure relates to the display of information relating to detected calcium such as a calcified portion of a blood vessel relative to one or more of angiography image or an optical coherence tomography image (or other intravascular image data).

In various embodiments, a proximal frame, a distal frame, and a frame disposed between them is displayed with detected calcium displayed using a first indicia, an angle or arc measurement of the detected calcium, including a sum of calcium arcs and angles in some embodiments, is also displayed numerically and/or with an indicia or graphic element, and an EEL detection is also displayed with a thickness measurement associated therewith. In various embodiments, the proximal frame and distal frame may be a first frame and a second frame or vice versa. The frame disposed between the first and second frames may be a third frame/intermediate frame, such as a user selected frame. In various embodiments, as shown in figures, Fr. Followed by a number indicates a particular frame number of an imaging pullback, such as an OCT, IVUS, OFDI, or other pullback generating imaging modality.

In one general aspect includes performing lumen detection to detect lumen boundary, calcium and EEL and display it relative to one or more arterial representation as part of a treatment, planning, review or other workflow disclosed herein. In one embodiment, detected lumen boundary data, such as on a per image basis. Other embodiments of this aspect include corresponding computer systems, apparatus, and computer programs recorded on one or more computer storage devices, each configured to perform the actions of the methods.

Implementations may include one or more of the following features. In one embodiment, inputting the detected lumen boundary data reduces waiting period for classifying regions and features of interest in image data. Implementations of the described techniques may include hardware, a method or process, or computer software on a computer-accessible medium. Various machine learning, image processing-based techniques, and other image analysis techniques may be used to automatically perform detection and segmentation of the features and regions of interest disclosed herein.

One general aspect includes a data collection and/or imaging and region/feature characterization system. The system also includes a housing. The system also includes a frame grabber to receive one or more of image data, such as polar data, ultrasound data, optical image data, x-ray image data and intravascular image data. The intravascular system also includes a power supply. The intravascular system also includes one or more electronic memory storage devices in electrical communication with the power supply. The intravascular system also includes one or more image processing software modules executable on the processor and stored in the one or more electronic memory storage devices. The intravascular system also includes a computing device includes a first processor, the computing device in electronic communication with the power supply and the first processor. In one embodiment, one more AI processors and dedicated AI processor memory is disposed in the housing or connected thereto through one or more ports, busses, or networks. In one embodiment, a given machine learning system (MLS) and its trained neural network is operated remotely, such as through a client/server implementation, an edge computing implementation, or a cloud or software as a service implementation.

In one embodiment, the system also includes one or more software programs stored in the one or more electronic memory storage devices. The system also includes a machine learning system includes a neural network includes one or more machine learning software modules. The intravascular system also includes one or more AI processors, wherein the one or more machine learning software modules are executable on the one or more AI processors; a bus; AI processor memory; an interface to send and receive image data from the first processor, the machine learning system in electronic communication with the power supply, wherein the machine learning system, the computing device, and the one or more electronic memory storage devices are disposed in the housing. In one embodiment, the bus is a PCIe bus. Other embodiments of this aspect include corresponding computer systems, apparatus, and computer programs recorded on one or more computer storage devices, AI processors, specialized ASICS, circuitry and circuitry components, each configured to perform the actions of the methods. In one embodiment, the bus connects the AI processor and on board memory and processor of diagnostic/imaging system.

Implementations may include one or more of the following features. The system wherein the housing, is the housing of an optical coherence tomography imaging system, OFDI system, tomography system, CT scan, x-ray or an intravascular ultrasound imaging system. The system wherein the one or more image processing software modules includes one or more of: tissue classification overlay software to label regions or features of interest when displayed to an end user, lumen detection software modules, and logic to regulate display of graphical user interfaces organized on a per workflow basis. The system wherein the one or more machine learning software modules includes one or more of: a neural network interface, lumen contour prediction, side branch prediction, calcium detection, EEL detection, user interface and input processing software modules, MLS interface software modules to control and set parameters for neural network, MLS memory manager software, pre-processing software modules, stent strut prediction software modules, jailed stent prediction software modules, guidewire prediction software modules, and interface modules for exchanging data with imaging system and workflow logic to display any of the foregoing relative to a given computer-directed or computer-support workflow. Implementations of the described techniques may include hardware, a method or process, or computer software on a computer-accessible medium.

In part, the disclosure relates to computer-based methods, and systems suitable for evaluating image data from a patient on a real time or substantially real time basis using machine learning (ML) methods and systems. In various embodiments, a set of image data, such a pullback of intravascular data is classified using a trained neural network such as a convolutional neural network on a substantially real time basis. In various embodiments, the set of image data includes between about 400 frames to about 600 frames. Further, given the use of rotating probes to obtain image data for OCT, IVUS, and other imaging data, dealing with the two coordinate systems associated therewith creates challenges. The present disclosure addresses these and numerous other challenges relating to solving the problem of quickly imaging and diagnosis a patient such that stenting and other procedures may be applied during a single session in the cath lab. The workflows disclosed herein are designed to display information in a controlled manner to reduce operator fatigue and expedite decision making while a patient is in the cath lab and available for or undergoing a treatment/diagnosis, deployment, review, or other workflow as part of a given procedure. The ability to perform segmentation of an image into multiple features or regions of interest and the use of directed workflows reduces the time a patient spends during the initial diagnostic procedures and subsequent treatment procedures by providing clinician with diagnostic information to inform stent planning, evaluation of bypass, atherectomy, debulking of stent deployment zones and other surgical options, and to assess changes in patient condition over time.

In part, the disclosure relates to a method for identifying regions of interest in a blood vessel that can include tissue types and other features such as side branches, stents, EEL, calcium, calcium angle, EEL, EEL thickness, guidewires and other features, characteristics and materials of the blood vessel that uses an imaging processing pipeline to detect the foregoing and uses a neural network to detect other regions or features of interest such as calcium, lumen, media, intima, lipid, and others disclosed herein.

In one embodiment, the tissue type or tissue characteristic, region of interest feature of interest, classes or types or blood vessel feature selected for segmentation and/or detection and representation in one or more mask, images, or outputs includes one or more of the following cholesterol, fiber, lipid pool, lipid, fibrofatty, calcification, calcium nodule, calcium plate, intima, thrombus, foam cells, proteoglycan, and others as disclosed herein. The various systems disclosed herein are operable to perform all of the methods and processes disclosed herein using specialized circuits, controllers, FPGAs, AI processors and other components as disclosed herein.

The methods disclosed herein may further include classifying the one or more regions or features of interest for each polar image as a type or class. In one embodiment, the type or class is selected from the group includes intima, media, adventitia, lumen, EEL, IEL plaque, calcium, calcium plaques. In one embodiment, the image data used with systems and methods disclosed herein includes carpet view images, scan lines, pixels, 2D images, 3D images, angiography images, intravascular images, CT scan images, x-ray images, and other images of arteries, veins, organs or other components of the circulatory system. The foregoing features, regions, channels, classes, etc. may be detected using a neural network trained relative thereto.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation.

BRIEF DESCRIPTION OF DRAWINGS

The patent or application file contains at least one drawing executed in color. Copies of this patent or patent application publication with color drawing(s) will be provided by the Office upon request and payment of the necessary fee.

The figures are not necessarily to scale, emphasis instead generally being placed upon illustrative principles. The figures are to be considered illustrative in all aspects and are not intended to limit the disclosure, the scope of which is defined only by the claims.

DETAILED DESCRIPTION

Figure 1:
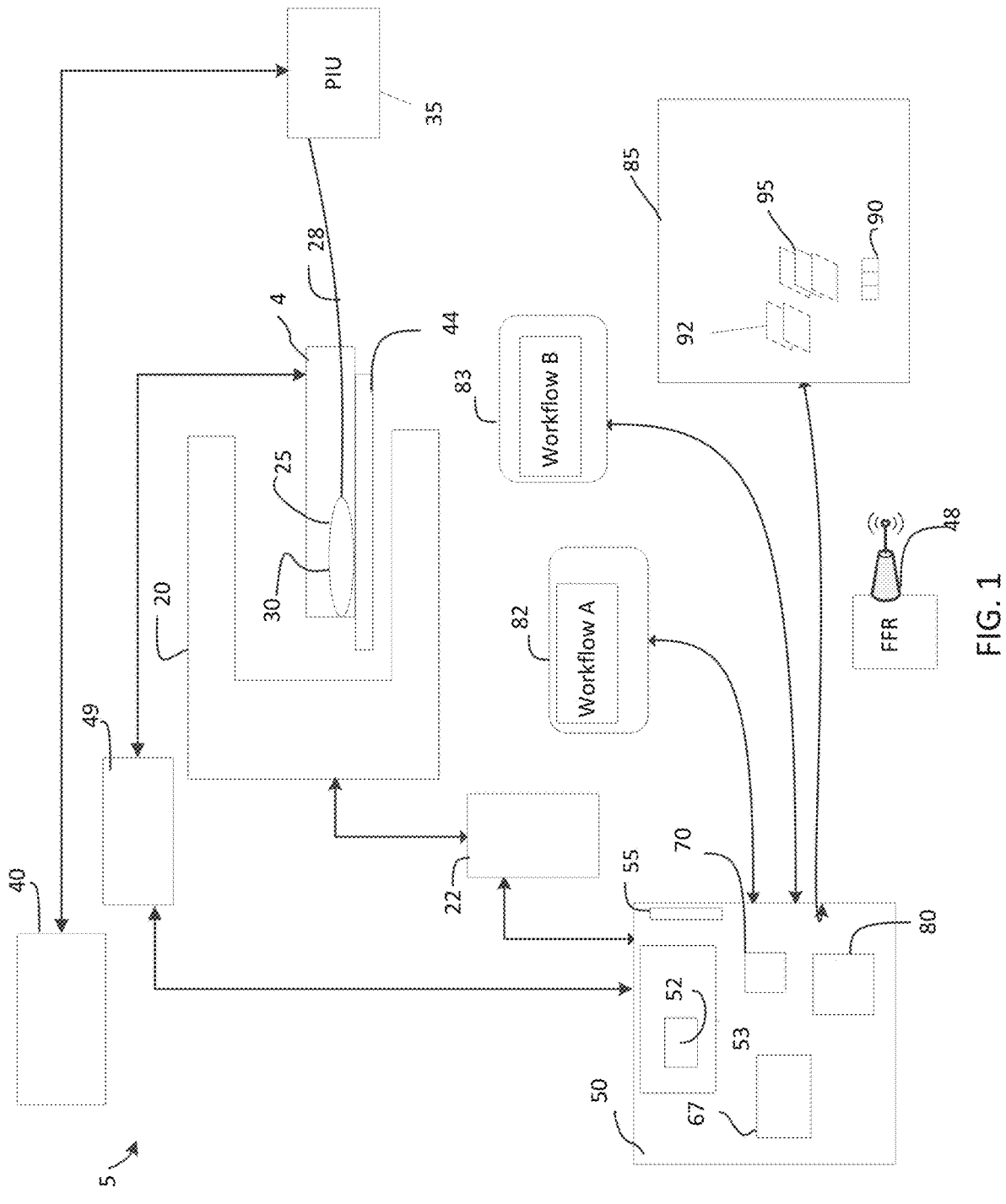
FIG. 1 is a schematic diagram of a diagnostic system suitable for imaging an artery, automatically detecting features/regions of interest relative to image data obtained, and display of enhanced directed workflows to streamline operations in a cath lab according to an illustrative embodiment of the disclosure.

In part, the disclosure relates to diagnostic systems that collect and/or store data, detected parameters, or images in electronic memory relating to an artery. In one embodiment, the systems facilitate the automated detection, determination of various metrics relative thereto to aid various diagnostic objectives, and/or display the forgoing to end users via various graphical user interfaces. These objectives may include, without limitation, stent sizing, stent deployment, balloon sizing, balloon deployment, review of concurrent or prior treatments or diagnostic procedures and other diagnostic tools, measurements and calculations. The user interfaces and associated diagnostics systems can include and/or be linked to received data from various imaging modalities such as x-ray imaging, CT scans, angiography (angio) systems, fluoroscopy systems, ultrasound systems, optical coherence tomography systems, intravascular imaging systems, combinations of the forgoing, and other imaging and diagnostic modalities.

In one aspect, the disclosure relates to various workflows that streamline cath lab procedures and make information easily accessible to a user, such as a cardiologist or other clinician. Each workflow includes representations of an artery segment that have been modified to include indicia such as color, hatching, dotted lines, overlays etc., to cause various detections of interest, such as calcium, EEL, lumen, lumen boundary, and others as disclosed herein to stand out and be identified across differing arterial representation or views such a cross-sectional or longitudinal views. In some embodiments, representations of an artery are symmetric about an axis such as longitudinal views. In various embodiments, color is used as an indicia such as the orange color shown various drawings to emphasize a feature of interest across various representations.

Various data collection and analysis systems are available to obtain information with regard to the coronary system. The data obtained using a device from a blood vessel or derived data from intravascular or extravascular measurements associated therewith can be analyzed or displayed to assist researchers and clinicians. In addition, various computer directed workflows or computer-support workflows can be generated and displayed in a prescribed manner to facilitate operator review of automatic detections of intravascular features pursuant to a morphology workflow, evaluating pre-treatment options and stent size selection pursuant to a sizing/planning workflow, selecting landing zones and evaluating an arterial segment as part of the selection pursuant to a deployment workflow and a reviewing stent deployment to assess stent expansion and malapposition to allow for further ballooning or other procedures to improve final stent deployment and expansion while patient is still in the cath lab.

Optical coherence tomography (OCT) is an imaging modality that uses an interferometer to obtain distance measurements relative to a blood vessel or objects disposed therein. In various embodiments, Optical Frequency Domain Imaging (OFDI) may also be used as an intravascular imaging modality. Intravascular ultrasound (IVUS) can also be used in probes to image portions of a blood vessel. Angiography systems and fluoroscopy systems are also often used to image a patient such that diagnostic decisions can be made and various possible treatment options such as stent placement can be carried out. These and other imaging systems can be used to image a patient externally or internally to obtain raw data, which can include various types of image data.

In general, the disclosure can apply to any intravascular data collection devices can be used to generate and receive signals that include diagnostic information, such as image data, relative to the blood vessel in which they are used. These devices can include without limitation imaging devices, such as optical or ultrasound probes, pressure sensor devices, and other devices suitable for collecting data with regard to a blood vessel or other components of a cardiovascular system. Prior to evaluating the various user interface representations and associated workflows, it is informative to consider an exemplary system for implementing the methods and artery assessment tools disclosed herein.

FIG. 1 is a schematic diagram of a diagnostic system 5 suitable for imaging an artery, automatically detecting features/regions of interest relative to image data obtained, and display of enhanced directed workflows to streamline operations in a cath lab. The system 5 supports various intravascular and non-intravascular imaging modalities to generate image data relative to an artery and present workflows to facilitate various diagnostic procedures and supporting various treatment options with evidence based measurements and the efficient display thereof.

The system 5 is suitable for viewing and assess a visual representation of arterial information. These user interfaces can include one or more moveable elements that can be controlled by a user with a mouse, joystick, or other control and can be operated using one or more processors and memory storage elements. Morphology results automatically obtained relative to image data can be displayed as part of a streamlined workflow.

During a stent delivery planning procedure, the levels and location of apposition the user can refer to OCT and annotated angiography to further expand or move a stent as part of delivery planning. These system features and methods can be implemented using system 5 shown in FIG. 1.

FIG. 1 shows a system 5 which includes various data collection subsystems suitable for collecting data or detecting a feature of or sensing a condition of or otherwise diagnosing a subject 4. In one embodiment, the subject is disposed upon a suitable support 44 such as table bed to chair or other suitable support. Typically, the subject 4 is the human or another animal having a particular region of interest 25.

The data collection system 5 includes a noninvasive imaging system such as a nuclear magnetic resonance, x-ray, computer aided tomography, or other suitable noninvasive imaging technology. As shown as a non-limiting example of such a noninvasive imaging system, an angiography system 20 such as suitable for generating cines is shown. The angiography system 20 can include a fluoroscopy system. Angiography system 20 is configured to noninvasively image the subject 4 such that frames of angiography data, typically in the form of frames of image data, are generated while a pullback procedure is performed using a probe 30 such that a blood vessel in region 25 of subject 4 is imaged using angiography in one or more imaging technologies such as OCT or IVUS, for example.

The angiography system 20 is in communication with an angiography data storage and image management system 22, which can be implemented as a workstation or server in one embodiment. In one embodiment, the data processing relating to the collected angiography signal is performed directly on the detector of the angiography system 20. The images from system 20 are stored and managed by the angiography data storage and image management 22.

In one embodiment system server 50 or workstation 85 handle the functions of system 22. In one embodiment, the entire system 20 generates electromagnetic radiation, such as x-rays. The system 20 also receives such radiation after passing through the subject 4. In turn, the data processing system 22 uses the signals from the angiography system 20 to image one or more regions of the subject 4 including region 25.

As shown in this particular example, the region of interest 25 is a subset of the vascular or peripherally vascular system such as a particular blood vessel. This can be imaged using OCT. A catheter-based data collection probe 30 is introduced into the subject 4 and is disposed in the lumen of the particular blood vessel, such as for example, a coronary artery. The probe 30 can be a variety of types of data collection probes such as for example an OCT probe, an FFR probe, an IVUS probe, a probe combining features of two or more of the foregoing, and other probes suitable for imaging within a blood vessel. The probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For a probe that includes an optical beam director, the optical fiber 28 is in optical communication with the probe with the beam director. The torque wire defines a bore in which an optical fiber is disposed. In FIG. 1, the optical fiber 28 is shown without a torque wire surrounding it. In addition, the probe 30 also includes the sheath such as a polymer sheath (not shown) which forms part of a catheter. The optical fiber 28, which in the context of an OCT system is a portion of the sample arm of an interferometer, is optically coupled to a patient interface unit (PIU) 35 as shown.

The patient interface unit 35 includes a probe connector suitable to receive an end of the probe 30 and be optically coupled thereto. Typically, the data collection probes 30 are disposable. The PIU 35 includes suitable joints and elements based on the type of data collection probe being used. For example, a combination OCT and IVUS data collection probe requires an OCT and IVUS PIU. The PIU 35 typically also includes a motor suitable for pulling back the torque wire, sheath, and optical fiber 28 disposed therein as part of the pullback procedure. In addition to being pulled back, the probe tip is also typically rotated by the PIU 35. In this way, a blood vessel of the subject 4 can be imaged longitudinally or via cross-sections. The probe 30 can also be used to measure a particular parameter such as a fractional flow reserve (FFR) or other pressure measurement.

In turn, the PIU 35 is connected to one or more intravascular data collection systems 40. The intravascular data collection system 40 can be an OCT system, an IVUS system, another imaging system, and combinations of the foregoing. For example, the system 40 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 40 can include ultrasound signal generating and processing circuitry, noise filters, rotatable joint, motors, and interface units. In one embodiment, the data collection system 40 and the angiography system 20 have a shared clock or other timing signals configured to synchronize angiography video frame time stamps and OCT image frame time stamps.

In addition to the invasive and noninvasive image data collection systems and devices of FIG. 1, various other types of data can be collected with regard to region 25 of the subject and other parameters of interest of the subject. For example, the data collection probe 30 can include one or more pressure sensors such as for example a pressure wire. A pressure wire can be used without the additions of OCT or ultrasound components. Pressure readings can be obtained along the segments of a blood vessel in region 25 of the subject 4.

Such readings can be relayed either by a wired connection or via a wireless connection. As shown in a fractional flow reserve FFR data collection system, a wireless transceiver 48 is configured to receive pressure readings from the probe 30 and transmit them to a system to generate FFR measurements or more locations along the measured blood vessel. One or more displays 82, 83 can also be used to show the various workflows disclosed herein, calcium angles, EEL detections, calcium detections, proximal frames, distal frames, and associated graphical user interfaces, EEL-based metrics, stent/no stent decisions, scores, recommendations for debulking and other procedures, evidence based recommendations informed by automatic detection of regions/features of interest, an angiography frame of data, an OCT frame, image data, stent planning interfaces, morphology interfaces, review interfaces, stent deployment interfaces, user interfaces for OCT and angiography data and other controls and features of interest. Two exemplary workflows, workflow A, and workflow B may be displayed on displays 82, 83 and may include any of the graphical user interfaces, panels, arterial images, arterial representations, features of interest, regions of interest, and other measurements and graphical elements disclosed or depicted herein, include any subsets thereof, without limitation.

The intravascular image data such as the frames of intravascular data generated using the data collection probe 30 can be routed to the data collection processing system 40 coupled to the probe via PIU 35. The noninvasive image data generated using image management system 22 can be transmitted to, stored in, and processed by one or more servers or workstations such as the co-registration server 50 workstation 85. A video frame grabber device 55 such as a computer board configured to capture the angiography image data from system 22 can be used in various embodiments.

In one embodiment, the server 50 includes one or more co-registration software modules 67 that are stored in memory 70 and are executed by processor 80. The server may include a trained neural network 52 suitable for implementing various embodiments of the disclosures. In one embodiment, an AI processor, such as a graphical processing unit, 53 is included in the server 50 and in electrical communication with memory 70. The computing device/server 50 can include other typical components for a processor-based computing server. Alternatively, more databases such as database 90 can be configured to receive image data generated, parameters of the subject, and other information generated, received by or transferred to the database 90 by one or more of the systems devices or components shown in FIG. 1.

Although database 90 is shown connected to server 50 while being stored in memory at workstation 85, this is but one exemplary configuration. For example, the software modules 67 can be running on a processor at workstation 85 and the database 90 can be located in the memory of server 50. The device or system use to run various software modules are provided as examples. In various combinations the hardware and software described herein can be used to obtain frames of image data, process such image data, and register such image data.

As otherwise noted herein, the software modules 67 can include software such as preprocessing software, transforms, matrices, and other software-based components that are used to process image data or respond to patient triggers to facilitate co-registration of different types of image data by other software-based components 67 or to otherwise perform annotation of image data to generate ground truths and other software, modules, and functions suitable for implementing various embodiments of the disclosure. The modules can include workflows, morphology workflow, review workflow, sizing workflow, deployment workflow, computer-directed workflow, computer-support workflow, lumen detection using a scan line based or image based approach, workflows, indicia generation, calcium angle/arc generation, stent detection using a scan line based or image based approach, indicator generation, apposition bar generation for stent planning, proximal/distal color coding/indicia generation, lumen boundary detection, stent expansion, lumen profile, target lumen profile, side branches and missing data, and others.

The database 90 can be configured to receive and store angiography image data 92 such as image data generated by angiography system 20 and obtained by the frame grabber 55 server 50. The database 90 can be configured to receive and store intravascular image data such as OCT image data, IVUS image data, or OFDI image data, or other non-intravascular arterial image data 95 such as image data generated by OCT system 40 and obtained by the frame grabber 55 of server 50.

In addition, the subject 4 can be electrically coupled via one or more electrodes to one more monitors such as, for example, monitor 49. Monitor 49 can include without limitation an electrocardiogram monitor configured to generate data relating to cardiac function and showing various states of the subject such as systole and diastole.

The use of arrow heads showing directionality in a given figure or the lack thereof are not intended to limit or require a direction in which information can flow. For a given connector, such as the arrows and lines shown connecting the elements shown in FIG. 1, for example, information can flow in one or more directions or in only one direction as suitable for a given embodiment. The connections can include various suitable data transmitting connections such as optical, wire, power, wireless, or electrical connections.

One or more software modules can be used to process frames of angiography data received from an angiography system such as system 22 shown in FIG. 1. Various software modules that can include without limitation software, a component thereof, or one or more steps of a software-based or processor executed method can be used in a given embodiment of the disclosure.

In part, the disclosure relates to intravascular data collections systems and related methods by which intravascular data collected by an intravascular probe can be transformed or analyzed by a processor-based system. The results of such analysis and transformation can be displayed to an end user in various representations such as a display that is in communication with a pipeline of imaging processing software modules for image segmentation/detection of features or regions of interest relative to image data, a machine learning system having a neural network to classify components of a medical image and detect instances of features and regions of interest, and other image processing and segmentation/detection systems. In one embodiment, a given imaging system, such as an OCT, IVUS, x-ray based imaging system is in electronic communication with an MLS and able to display modified versions of the image data obtained using a given type of imaging system during the same session when such image data was obtained. Various neural network architectures may be used for image segmentation such as V-net, U-net, CUMedVision1, CUMed-Vision2, VGGNet, Multi-stage Multi-recursive-input Fully Convolutional Networks (M²FCN) Coarse-to-Fine Stacked Fully Convolutional Net, Deep Active Learning Framework, ResNet, combinations thereof, and other neural networks and software-based machine learning frameworks suitable for image segmentation.

In one embodiment, the MLS includes a specialized hardware system to handle the necessary machine learning operations and training thereof processes such that results can be obtained on an expedited basis to support timely generation of workflows disclosed herein. The specialized hardware system of a given MLS embodiment can include a plurality of processors such as AI/ML processors. The machine learning system can be implemented by training a classifier to segment or operate upon an image such that its constituent tissues, tissues types, and other regions of interest are detected and characterized based on type or another parameter. In one embodiment, the lumen, intima, media and plaque are detected and identified as having boundaries corresponding to these different tissues.

The disclosure relates to an advanced machine learning system that includes one or more AI processors that include an increased amount of memory allocated on a per processor basis. The advanced machine learning system is designed to support a multi-channel segmentation approach. Various channels can be selected with regard to the different regions of interest and characteristics for a given implementation. For example, in one embodiment, a first channel, a second channel, a third channel and a fourth channel are specified such that one of each of the foregoing channels is associated with the lumen, calcium, EEL, and other regions or features of interest. Other classes/types can be associated with different channels to facilitate segmentation.

In one embodiment, the calcium is classified is classified relative to wall/tissue of artery surrounding the lumen. The lumen boundary detection can provide an outer boundary for calcium in the tissue of artery wall. In some embodiments, the plaque type may be classified as calcified. In addition, given that the present of calcium/a plaque and other detectable features of a given section of an artery can indicate the presence of a constriction such as from a stenosis, another feature of the disclosure is the ability to quickly and automatically obtain one or more scores associated with a given plaque or stenosis to help facilitate decision making by an end user. For example, a given score determined using the image data and the machine learning-based analysis thereof can help determine whether no immediate action is recommended, or if a stent should be placed relative to a stenosis, or if an atherectomy or other procedure such as bypass is warranted. This is performed as part of the workflows described herein such as the morphology work flow or as part of stent planning/sizing workflow. A calcium angle of greater than about 180 degrees and an EEL thickness of For a healthy patient, arteries have various layers arranged in a consistent structure that include the intima, media and adventitia. As a result of the process of atherosclerosis, the intima becomes pathologically thickened and may contain plaques composed of different types of tissues, including fiber, proteoglycans, lipid and calcium, as well as macrophages and other inflammatory cells. These tissue types have different characteristics when imaged using various imaging systems that can be used to establish a set of training data for one or more of the machine learning systems of the disclosure. The plaques that are believed to be most pathologically significant are the so-called vulnerable plaques that consist of a fibrous cap with an underlying lipid pool. Different atherosclerosis plaques have different geometrical shapes. For examples, the foam cells usually form ribbon-like features on the shoulders of large lipid pool; the media appears like annulus around the vessel, etc. The shape information is currently used in qualitative assessment of OCT images. In one embodiment, the neural net is trained to identify fibrous cap and/or fibrous cap with an underlying lipid pool. In various embodiments, references to calcium herein also include calcified plaques and other calcium containing tissue, without limitation.

The ability to quickly perform an imaging procedure on a patient and obtain arterial images and then processes the images using a machine learning system while the patient is still catheterized and prepared to receive a stent or other treatment option results in significant time savings and improvements in patient outcomes.

The media and the outer edge of the media called External Elastic Lamina or EEL are used by physicians to size their stent during intervention. Finding the media and measuring the diameter in a partly diseased tissue is time consuming and difficult. It also requires image interpretation training. Automatic detection and measurement of the EEL diameter addresses these technical challenges faced when diagnosis or otherwise evaluating a patient for treatment options. An example of the measurement of such a diameter is shown in FIGS. 3A-3D as part of the stent sizing workflow in which lumen diameter or another lumen distance and EEL diameter or another EEL distance can be reviewed by end users to size stents based on these arterial measures and candidate landing zones.

Figure 2A:
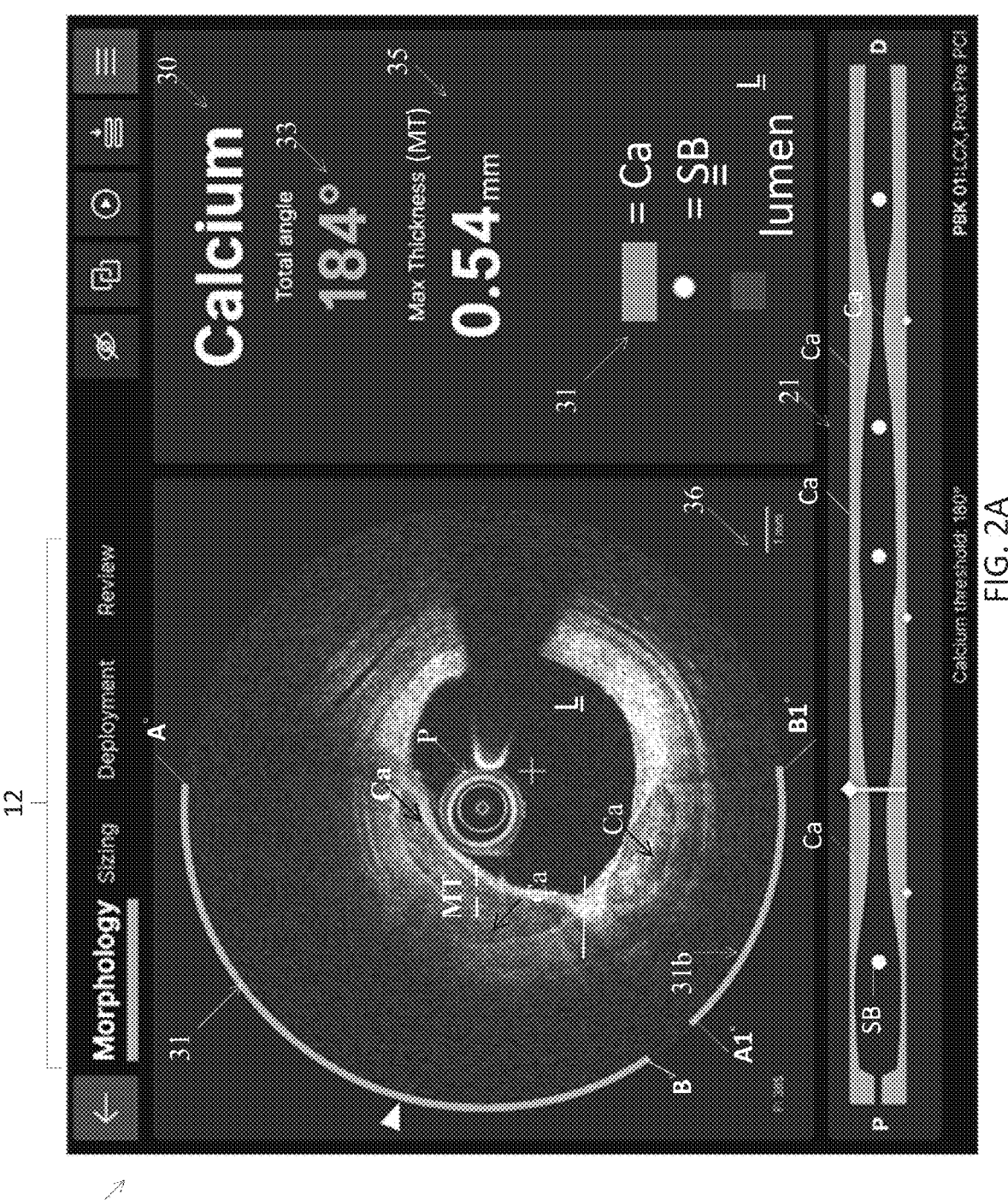
FIG. 2A is a an exemplary user interface suitable for assessing image data obtained and stored in memory, such as the system of FIG. 1 with various features of interest such as calcium detections, total calcium angle, proximal and distal frames and other features as shown according to an illustrative embodiment of the disclosure.
Figure 2B:
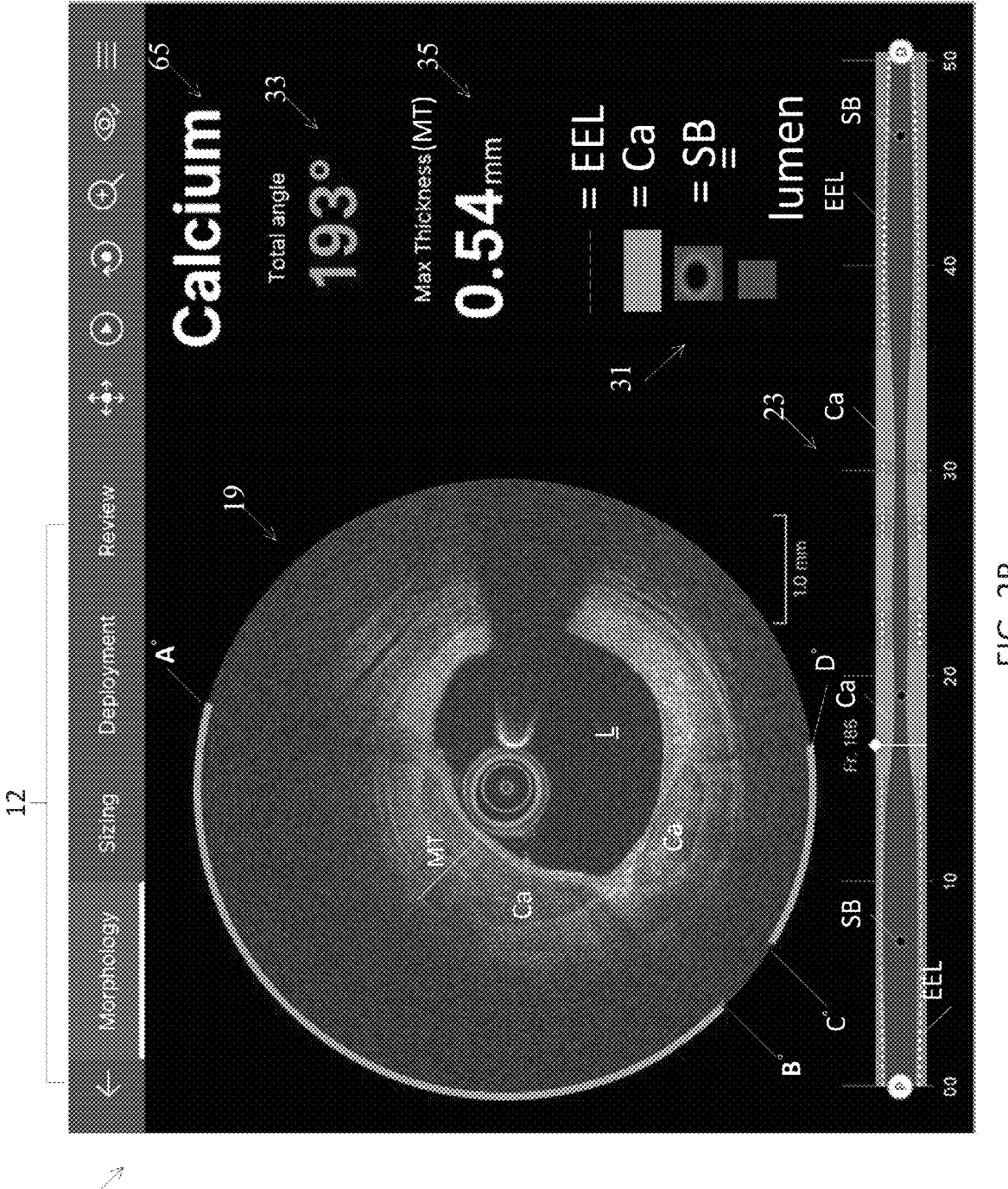
FIG. 2B is a an exemplary user interface suitable for assessing image data obtained and stored in memory, such as the system of FIG. 1 with various features of interest such as calcium detections, total calcium angle, EEL detections for multiple frames, proximal and distal frames and other features as shown according to an illustrative embodiment of the disclosure.

FIGS. 2A and 2B are exemplary graphical user interfaces of a diagnostic system suitable for displaying images and representations of one or more features of a blood vessel such as an artery. In particular, user interface 10 of FIG. 2A and user interface 15 of FIG. 2B show sectional views 17, 19, respectively of a portion of an artery on the right and a longitudinal view 21, 23 of a section of the respective artery at the bottom of the interface. Each of the cross-sectional views and longitudinal views are examples of representation of an artery, whether for one frame or multiple frames, respectively.

The longitudinal representation or images 21, 23 and others shown also include labels for the proximal direction P on the left side and the distal direction D on the right side. In one embodiment, the longitudinal mode of the vessel is derived from imaging data or other data collected such as measurements for a given artery being evaluated. In one embodiment, the actual images of the arterial segment are displayed. In other embodiment, smoothing, vectorization, or a simplified or visual data reduced representation of longitudinal views or other views including data shown relative thereto (see legend 31) are also generated.

In one embodiment, a device such as a probe P is disposed in artery as shown in FIG. 2A. In addition, the various views, such as longitudinal, cross-sectional, and otherwise can be individual frames of image data. Frame 120 of a pullback of probe P is shown in FIG. 2A and corresponds to the view 17 shown above and frame 120 shown below in the longitudinal view. Various scales and measurement references such as reference 36 corresponding to a scale such as an about 1 mm scale is also shown. Other scales and metrics can be used that relate or track arterial features and dimensions. The diagnostic system can include one or more computer-based imaging systems and include specialized subsystems for detecting features of a blood vessel.

The user interfaces disclosed herein can include various menus such as menu 12 and other menus, panels, panels, interfaces, controls, and combinations thereof. In one embodiment, various screens/user interfaces can be accessed through menu 12 relating to morphology, sizing (such as stent sizing or other arterial metrics), deployment (such as device or procedure deployment), co-registration, review of current or prior procedures or other diagnostic data, subject metrics, supporting imaging modalities, etc. In various embodiments, during stent planning workflow, end users can elect to side stent based on EEL measurements and/or lumen diameter measurements. This is shown in the graphical user interface of FIGS. 3A-3D.

Any suitable morphological features can be detected and displayed relative to an image of a blood vessel or other representations thereof. In one embodiment, the features detected are with regard to an artery. The systems and method described herein can display various representations and metrics relating to detected calcium and one or more arterial layers or measurements relating thereto. Some exemplary methods of detecting and displaying calcium relative to a blood vessel are described in more detail in U.S. Pat. No. 9,940,723 entitled "SYSTEMS AND METHODS TO DETECT AND DISPLAY ENDOVASCULAR FEATURES" filed on Dec. 14, 2015, the disclosures of which are incorporated by reference in their entirety.

In general, exemplary user interface 10, 15 are configured to display morphology information, although other information can be added and displayed with various indicia, overlays, and visualizations. Both the interfaces 10, 15 show calcium that has been detected in artery at one or more segments or frames. The top right part of each interface 10, 15 identifies calcium 65 as the morphological feature being emphasized. The legend 31 can be toggled on and off for various interfaces and shows dotted lines being indicative of EEL, a color such as orange corresponding to regions where calcium was detected on a threshold associated with calcium detection levels was met and/or exceeded in various embodiments, side branches (SB), and lumen (L), and other parameters can be shown with symbols and indicia such as color or hatching or other visual elements.

Calcium plaques in an artery are correlated with heart disease and present challenges when stenting relative thereto. Calcium deposition results in a narrowing of blood vessel diameter and also stiffens the blood vessel wall, which significantly reduces blood vessel performance. Calcium plaques therefore are one of the major targets of cardiovascular intervention. The user interfaces disclosed herein relative to calcium detections in an artery, calcium thickness, and calcium angle provide diagnostic information to end users that allow them to navigate calcified regions and make informed decisions about stenting relative thereto or elected to stent in a region with a thinner calcium region or elect to perform a de-bulking procedure such as an atherectomy or other tissue/material removal process.

In one embodiment, the disclosure relates to graphical user interfaces suitable for displaying the external elastic layer (EEL) of an artery or measurements or metrics obtained or generated using detected regions of EEL. For example, in one embodiment, detected regions of EEL or measurements or calculated values of EEL diameters or radii are displayed relative to a representation of an artery as dotted or broken line. Examples of a user interface displaying one or more of the foregoing EEL-based and Calcium parameters are shown in FIGS. 2A, 2B, 2C, 2, 4, 5A, 5B, and 6 in which a dotted line is used to display such a parameter. The legends used herein for Ca, EEL, etc. apply other figures as applicable, if a legend is not shown with such a figure. In various embodiment, an orange color is shown in the figures to indicate calcium, stent expansion level, or stent malapposition as informed by context of a given figure.

Figure 2C:
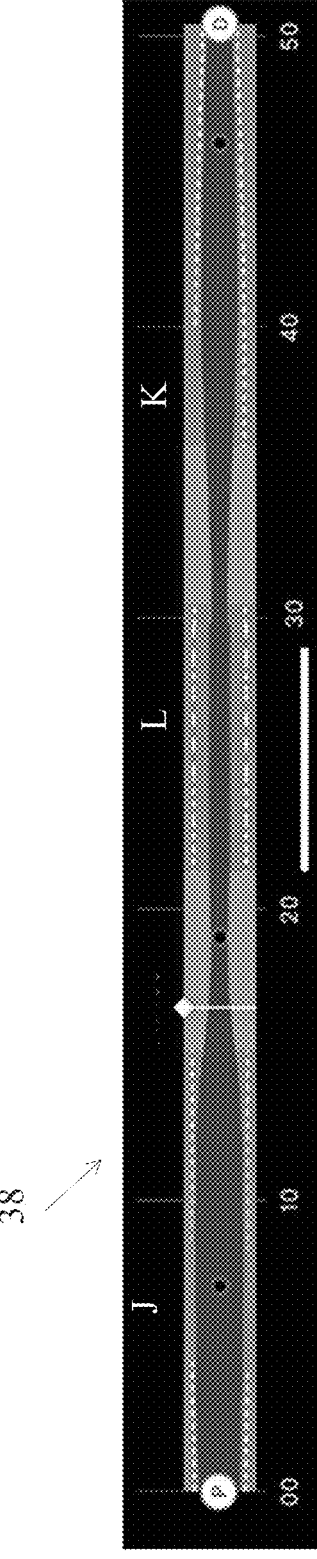
FIG. 2C is an exemplary user interface of a longitudinal view of an artery in which some of the EEL regions are below a threshold in various regions according to an illustrative embodiment of the disclosure.
Figure 2C:
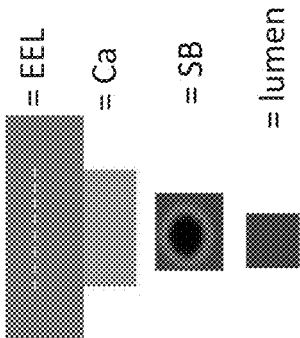

FIG. 2C shows an exemplary user interface of a longitudinal view of an artery in which some of the EEL regions are below a threshold as shown in regions J and K. In addition, regions of calcium Ca are also shown by orange colored region. The absence of the dotted line in regions J and K indicates that plaque may have overgrown those regions and the EEL is not detected or not detected at a level that satisfies the threshold to depict it. In this way, the user interface 38 helps an end user identify regions to avoid when selecting landing zones. In addition, region L, is shown with different dotted line spacing. This is an example of how other thresholds can be set to show how EEL changes along the length of an artery and a representation thereof generated by diagnostic system embodiments. These changes can be used to guide decision making based on EEL variations.

In one embodiment, diagnostic system and related user interfaces can be interacted with by an end user via various input devices such as a touch screen, joystick, trackball, mouse, keyboard, combinations thereof. The systems and methods relate to the detection, displaying, manipulation, transform, and visualization of calcium, EEL, EEL metrics, EEL diameter, EEL radius, EEL derived values, landing zones, stent landing zones, balloon landing zones, target zones, stenosis, lesions, reference frames, marker bands, regions of stent malapposition, thresholds, deviations or difference relative to thresholds, stent expansion metrics, malapposition thresholds, stent expansion thresholds, calcium arc lengths, calcium angular measurements, circumferential measurements, The user interface may include one or more images or representations of an artery from various viewing angles and sectional views. In one embodiment, EEL positions, diameters thereof, or other EEL-based parameters are shown relative to angular measurement or detected calcium arc that can be shows as total angle in degrees 33 as shown in FIGS. 2A and 2B. The arc, angular measure, or circumferential range of calcium detected relative to a given section of an artery can be shown as an arc length or angular ranges or via other metrics. In FIG. 2A, the detected Calcium (Ca) 65, is shown having an angular range from angle A degrees to B degrees. In addition, another calcium arc is shown from A1 to B1. The total angle for calcium is the sum of arcs 31 and 31*b*. Specifically, in FIG. 2A, this total angle is shown as 76 degrees. In addition, a max thickness value MT for the detected calcium 65 (Ca) is also shown. In this example, the MT is about 0.37 mm. The detected calcium is also shown in the longitudinal view 21 relative to the EEL parameter.

In FIG. 2B, two regions of calcium are shown in interface portion 19. The angular range of the first calcium region is from A degrees to B degrees and the second calcium region is from C degrees to D degrees. In one embodiment, two different total Ca angles can be shown. In FIG. 2B, the sum of the ranges for angles A to B and C to D are combined with total angle of 193 degrees 33. The max thickness MT for the calcium region disposed between A degrees and B degrees is also shown and has a value of about 0.54 mm. In various embodiments, a calcium angle greater than 180 degrees is identified to help inform user decision making as suitable for de-bulking or stenting based on that factor and calcium thickness.

In one embodiment, when selecting landing zones to deploy a particular stent or balloon, the diagnostic user interface described herein can indicate to an end user when additional vessel prep is needed or areas to avoid for landing zones. FIG. 2C shows show regions J and K where landing zones should be avoided. Region L of the arterial representation 38 shows EEL based values such as diameter values that change across the regions based on the dotted line label changes.

Figure 2D:
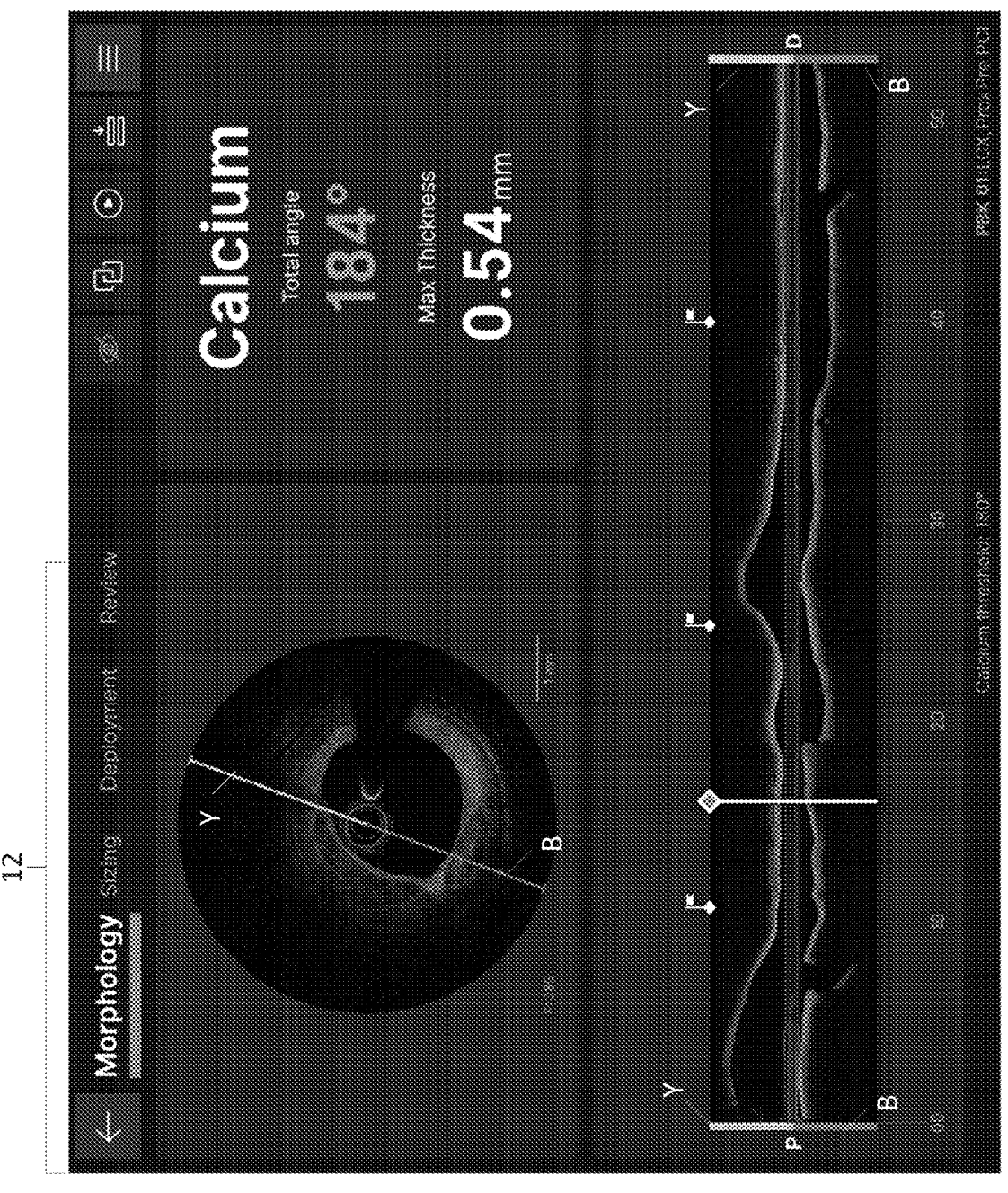
FIG. 2D is a an exemplary user interface of morphology workflow in which various panels are arranged as part of the user interface to show various bookmarks and orientation of artery in cross-sectional representation of artery relative to longitudinal representation of artery according to an illustrative embodiment of the disclosure.
Figure 2E:
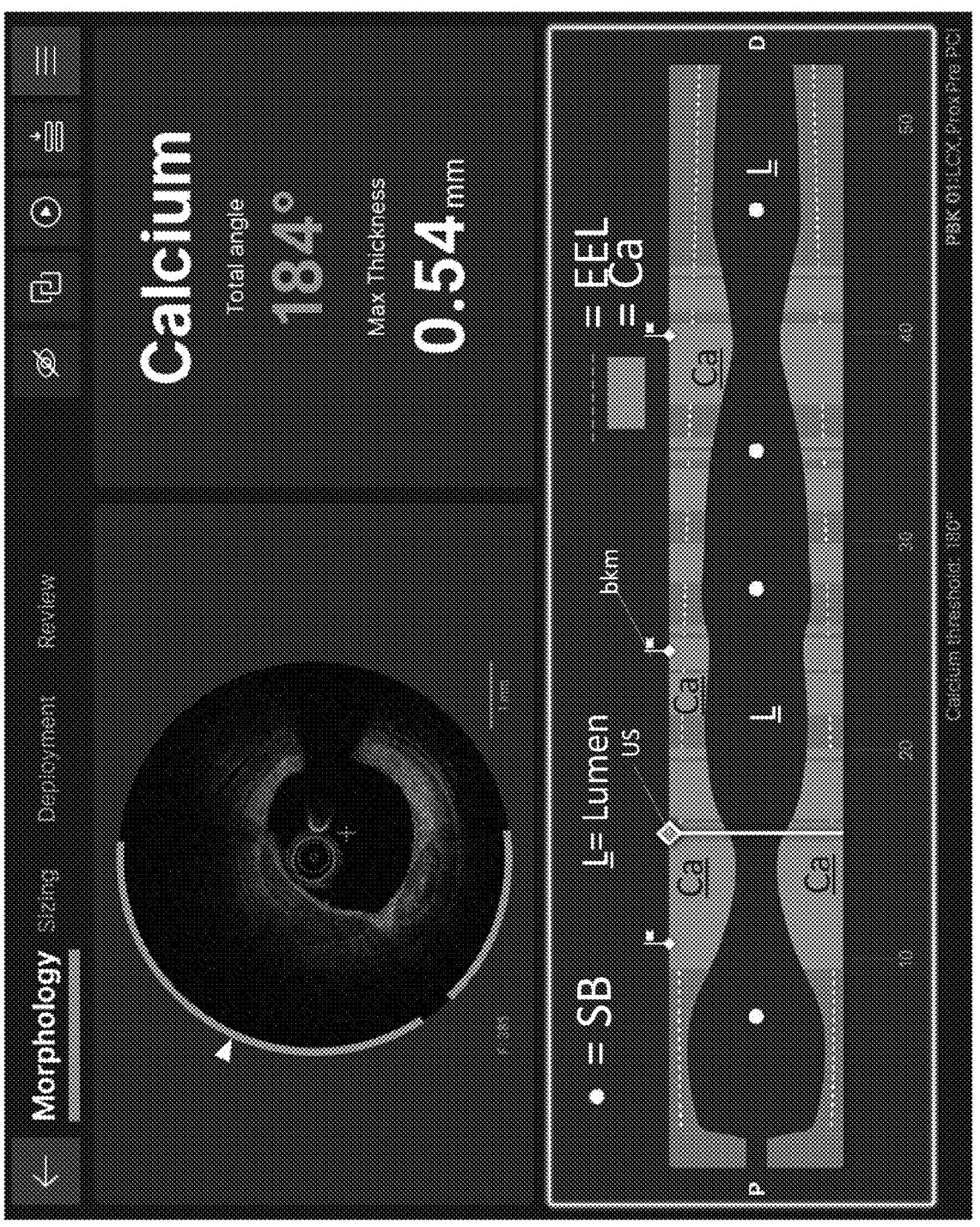
FIGS. 2E and 2F are exemplary graphical user interfaces suitable for implementing a morphology workflow in which calcium and EEL detections and associated measurements are depicted.
Figure 2F:
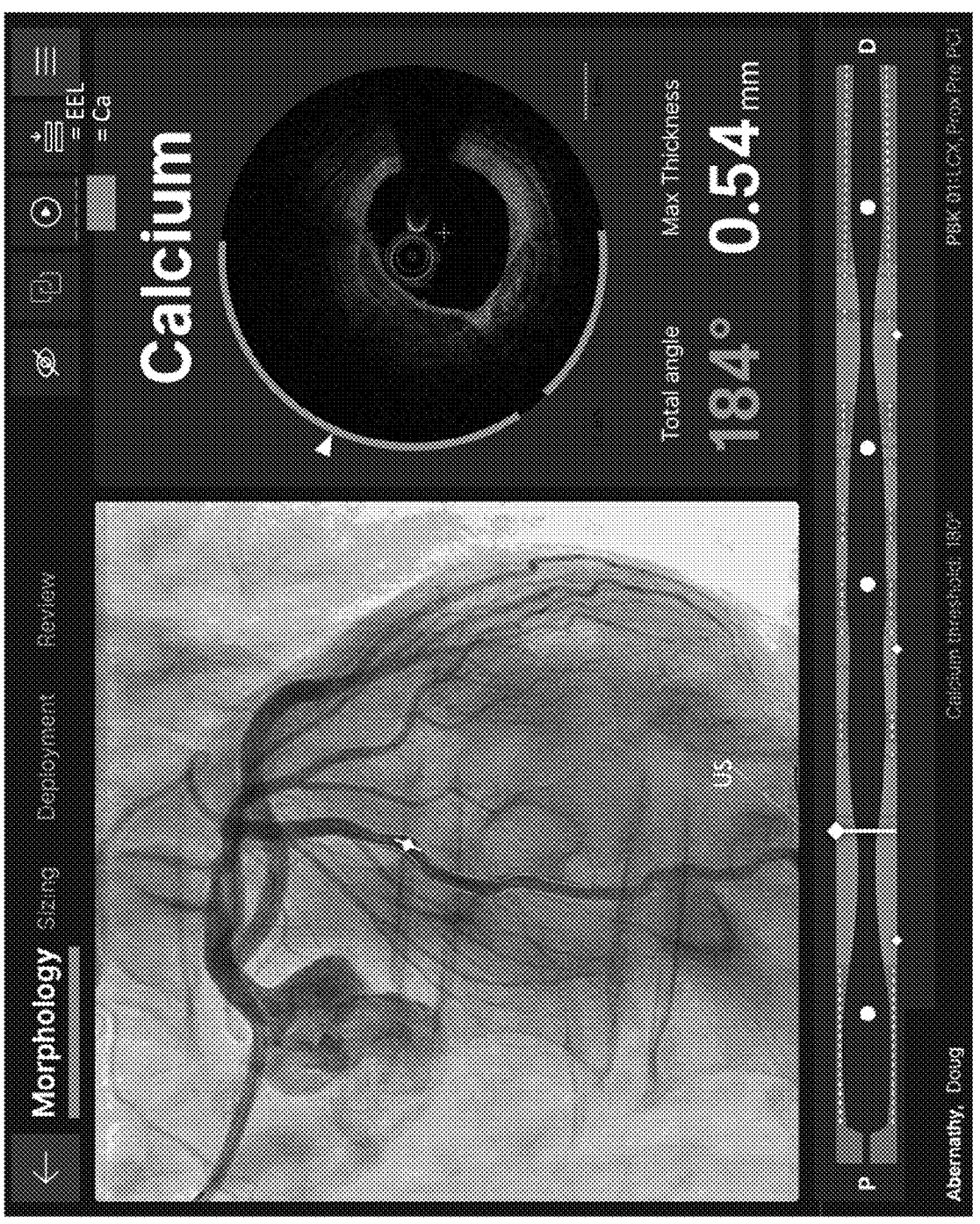

FIG. 2D is a an exemplary user interface of morphology workflow in which various panels are arranged as part of the user interface to show various bookmarks and orientation of artery in cross-sectional representation of artery relative to longitudinal representation of artery. In FIG. 2D, the proximal and distal reference frame are identified with an indicia, in this case, the colors yellow Y and blue B. The top portion of the distal reference and proximal reference frame is yellow and the bottom portion is blue. This orientation maintaining features is also used in FIG. 3B. These identified frames, distal and proximal show which part of the artery is being viewed in the upper panel of the graphical user interface that maintain the Y, B orientation of the proximal and distal reference frame. Also, as part of this morphology work flow a total calcium angle of 184 degree and maximum thickness MT of calcium 0.54 mm is also shown. The various flags in the longitudinal mode are bookmarks that let a user move back and forth between previously identified frames of interest.

Further, automated EEL measurements and lumen measurements such as EEL and lumen diameters shown in FIGS. 3A-3D and detected using system of FIG. 1 using a MLS or other detection system help inform what stent size to consider and what type of stent should be used. Calcium detection via MLS provides info on lesion preparation and treatment choices, such as selecting atherectomy over stenting. In addition, calcium detection provides an input parameter when deciding between an atherectomy procedure as well as when selectin a given vendor's stent, stent type, stent model, stent length, and stent thickness. The interactions with graphical user interfaces support a workflow by which users can move and change various dimensions relative to the imaged artery and have greater flexible when selecting a stent and where it will be deployed.

In one embodiment, the dotted line in one or more views, such as a longitudinal view, shows EEL diameter. Detecting the EEL on a per frame basis, per vessel segment basis, or subsets and combinations of the foregoing can be implemented using image processing, machine learning, artificial intelligence, neural networks, and other techniques as disclosed herein.

In some arteries, once plaque is growing or otherwise in place, it can push out or surround the EEL. As a result, in some embodiments, the dotted line corresponding to EEL threshold metric such as detecting an EEL or determine that an EEL diameter threshold value has been met or exceeded can result in regions in which the dotted line or other indicia for an EEL detection is present and absent on an intermittent along a given segment of the artery. This can indicate regions that are poor candidates for stent or balloon landing zones because of plaque placement eclipsing or otherwise obscuring the EEL such that the EEL-based parameter is not detected for a given region, frame, frames or segment. Thus, breaks in the indicia, such as a dotted line, indicative an EEL parameter detection can indicate regions to be avoided from a landing zone/deployment perspective. The use of three frames, including a user selectable frame, help with sizing workflow to expedite decision making. One or more markers on longitudinal mode can be changes to vary middle frame shown 153.

In one embodiment, the orange indicia associated with calcium detection is displayed when a particular threshold for calcium has been detected such as for a certain threshold thickness being satisfied for detected calcium or for a given circumferential percentage or arc length or angle span for detected calcium. When the value for such as threshold is met or for meeting different thresholds, one or more indicia associated with satisfying the threshold requirements for calcium can be displayed. Any suitable indicia such as hatching, colors, animations, and others can be used for any of the arterial features suitable for display relative to the disclosed user interfaces and subsets thereof. In one embodiment, the various thresholds for detecting particular features and when and how to display them relative to the interface are specified by an end user via an input user interface. In other embodiment, the threshold values can be pre-set or various pre-set value can be provided for user selection.

Figure 3A:
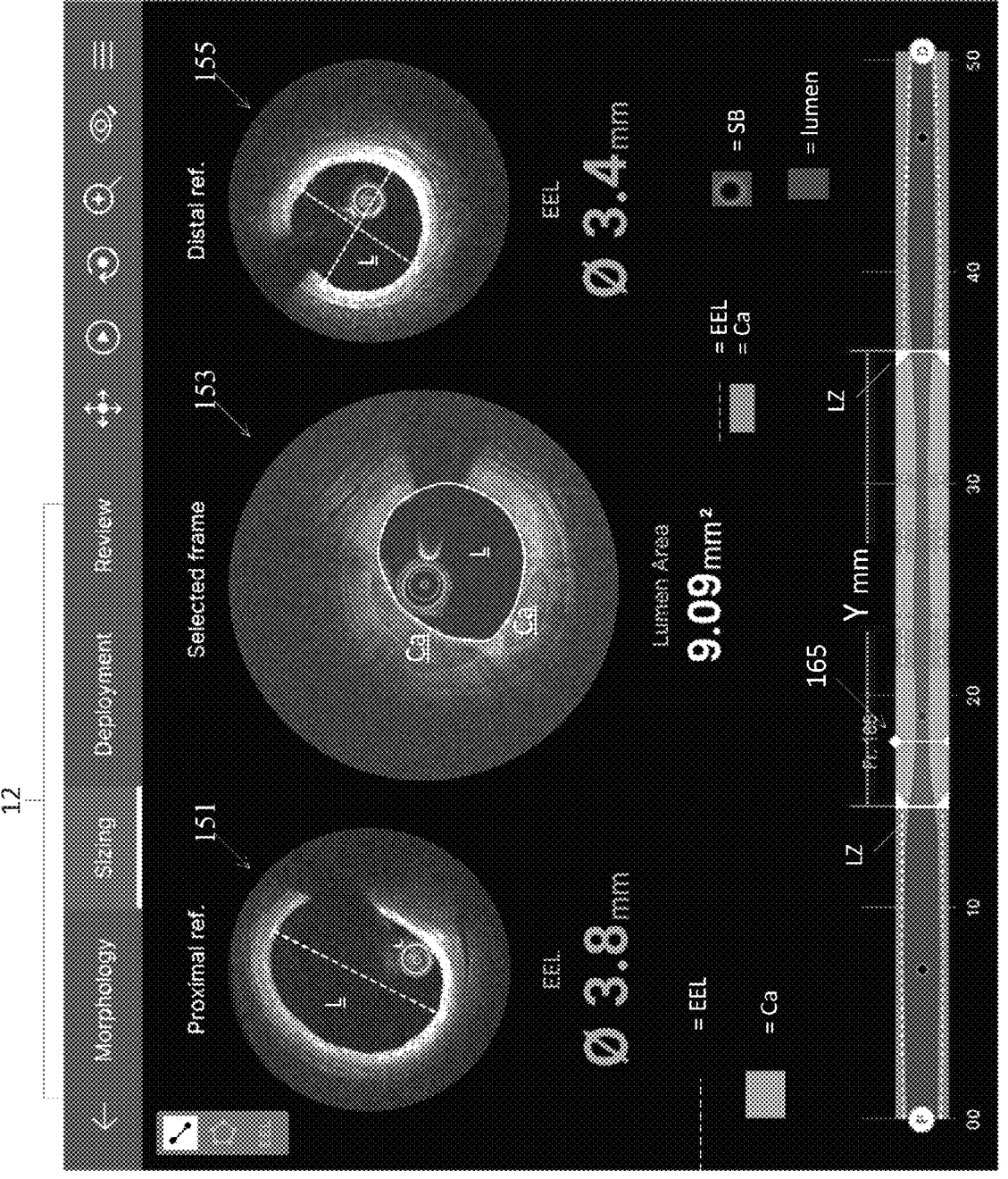
FIGS. 3A-3D are exemplary graphical user interfaces suitable for implementing a stent sizing workflow for selecting a stent and other stent parameters such as stent length relative to representations of the artery suitable for evaluating stent landing zones according to an illustrative embodiment of the disclosure.

FIG. 3A shows a graphical user interface of a stent sizing workflow. In the upper portion of the interface, there three views in the top portion of the figure that corresponding to frames or particular views or slices of artery at proximal reference 151, the selected frame 153 (which corresponds to frame with diamond in bottom longitudinal view 165) and a view at distal reference frame 155.

The view in lower portion of FIG. 3A shows a combined Ca and EEL in Lumen Profile view. The proximal and distal references 151, 155 shows lumen L with one or more dotted lines passing through lumen L. These values from measuring these lines are applied to measured or detected EEL positions, points, or pixels and are used to generate a measured EEL diameter or an average EEL diameter. Some exemplary EEL diameter measure is shown as about 3.8 mm (proximal) and about 3.4 (distal).

Figure 4A:
FIG. 4A shows an exemplary co-registration interface suitable for configuring and demonstrating intravascular and angiography co-registration in support a stent deployment workflow according to an illustrative embodiment of the disclosure.

FIG. 4A shows an exemplary co-registration interface 200. In one embodiment, angiography data is obtained such as angiography images while another imaging modality is also used such as OCT, IVUS, x-ray, etc. The angiography data can be used to co-register other data with the other imaging modality, such as OCT, IVUS, etc. The path of the pullback is shown with path in artery. Starting point of contrast cloud 207 may also be shown.

Figure 4B:
FIGS. 4B- and 4C are exemplary graphical user interfaces suitable for implementing a stent deployment workflow according to an illustrative embodiment of the disclosure.
Figure 4C:
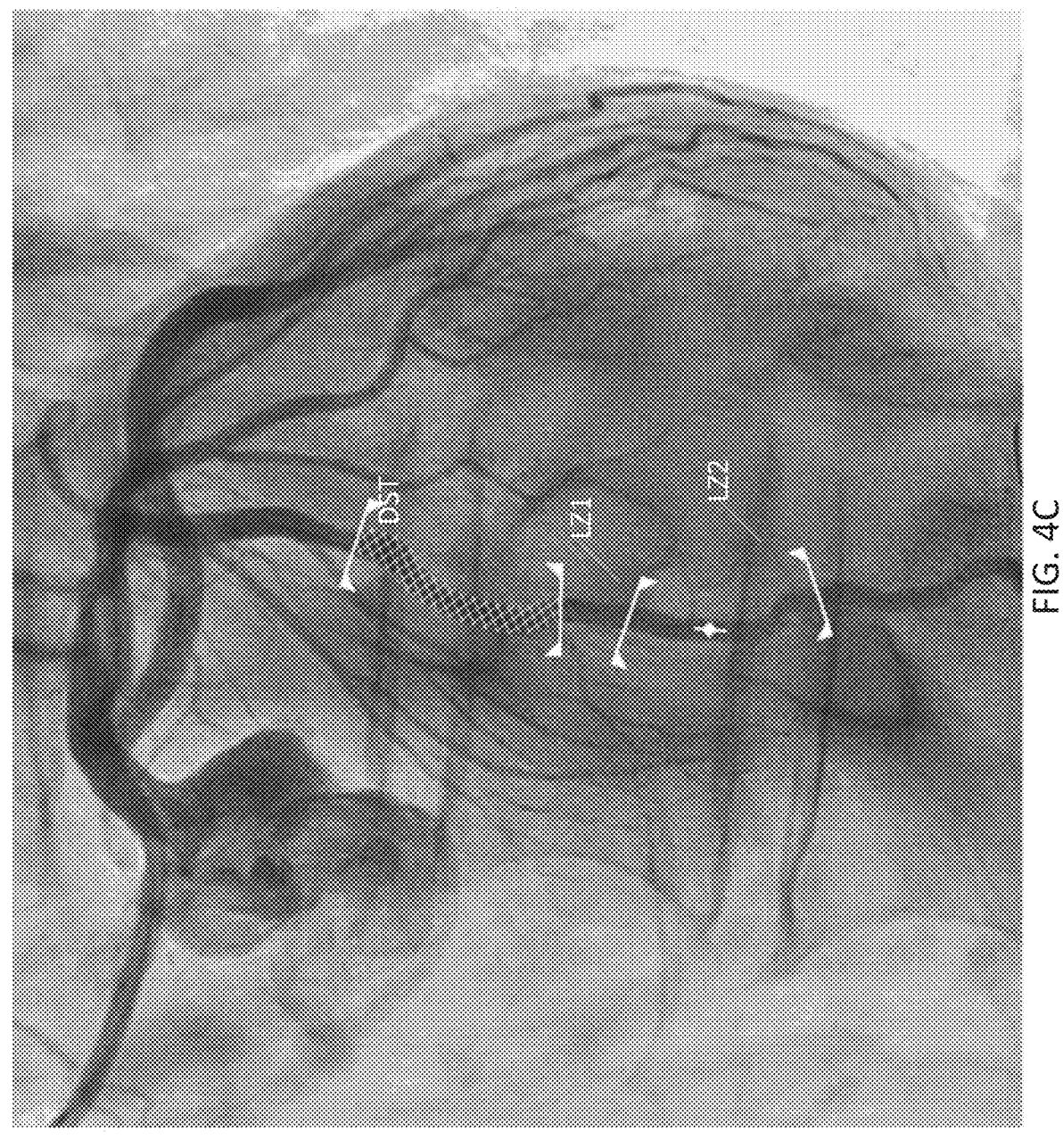

FIG. 4B shows a user interface 153 that has live angio on the left and positions it next to reference angiography on the right which has been co-registered with another imaging modality such as OCT, IVUS, x-ray, etc. This dual arrangement of live and reference angiography information helps a user visualize artery relative to angiography that is co-registered to OCT or other imaging modality. This can be used to help deploy a stent or balloon with the reference co-registered data informing the live angiography. FIG. 4C shows an angiography image that has been co-registered with an OCT image such that an existing deployed stent DST is shown and two landing zones LZ1, LZ2 selecting during stent planning workflow or another work flow are displayed on the angiography image although originated from an workflow interface in which intravascular or other image data was used to select and plan stent deployment.

Various endpoints, such as landing zones can be shown on angiography such as end points S and T. These points map or track with corresponding points below such that a morphological mapping between an artery representation can be linked, mapped, or otherwise co-registered relative to angiography data such as images or centerlines or other related data. These can be used to select stent landing zones as part of deployment process. In addition, measurements of distances, such as the distance Y mm can be evaluated to select or try different stent lengths ad part of stent deployment planning stage.

Figure 5A:
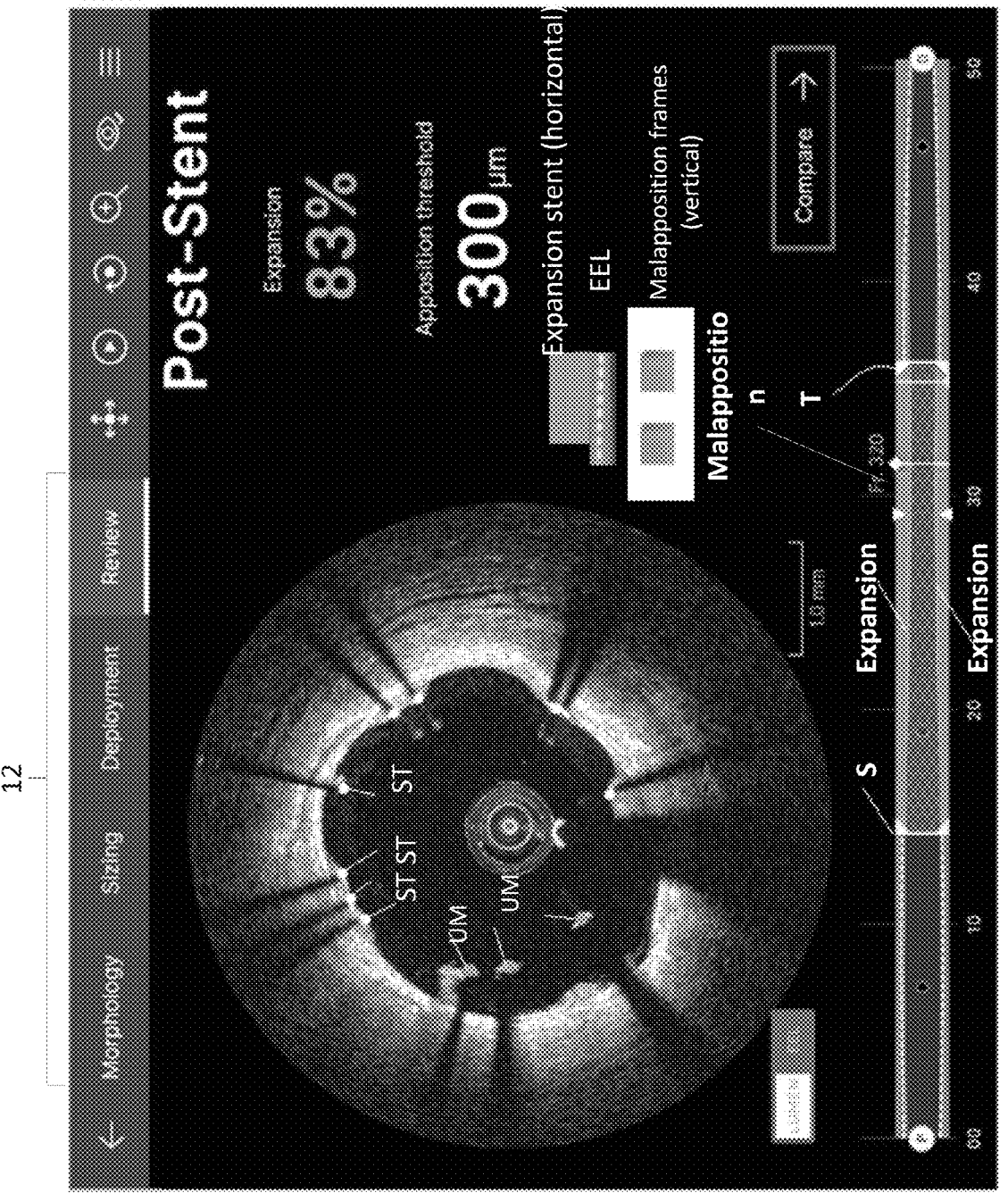
FIGS. 5A-8 are exemplary graphical user interfaces suitable for implementing a review workflow by which additional procedures such as additional ballooning or other stent re-deployment may be performed to improve patient outcomes according to an illustrative embodiment of the disclosure.
Figure 5B:
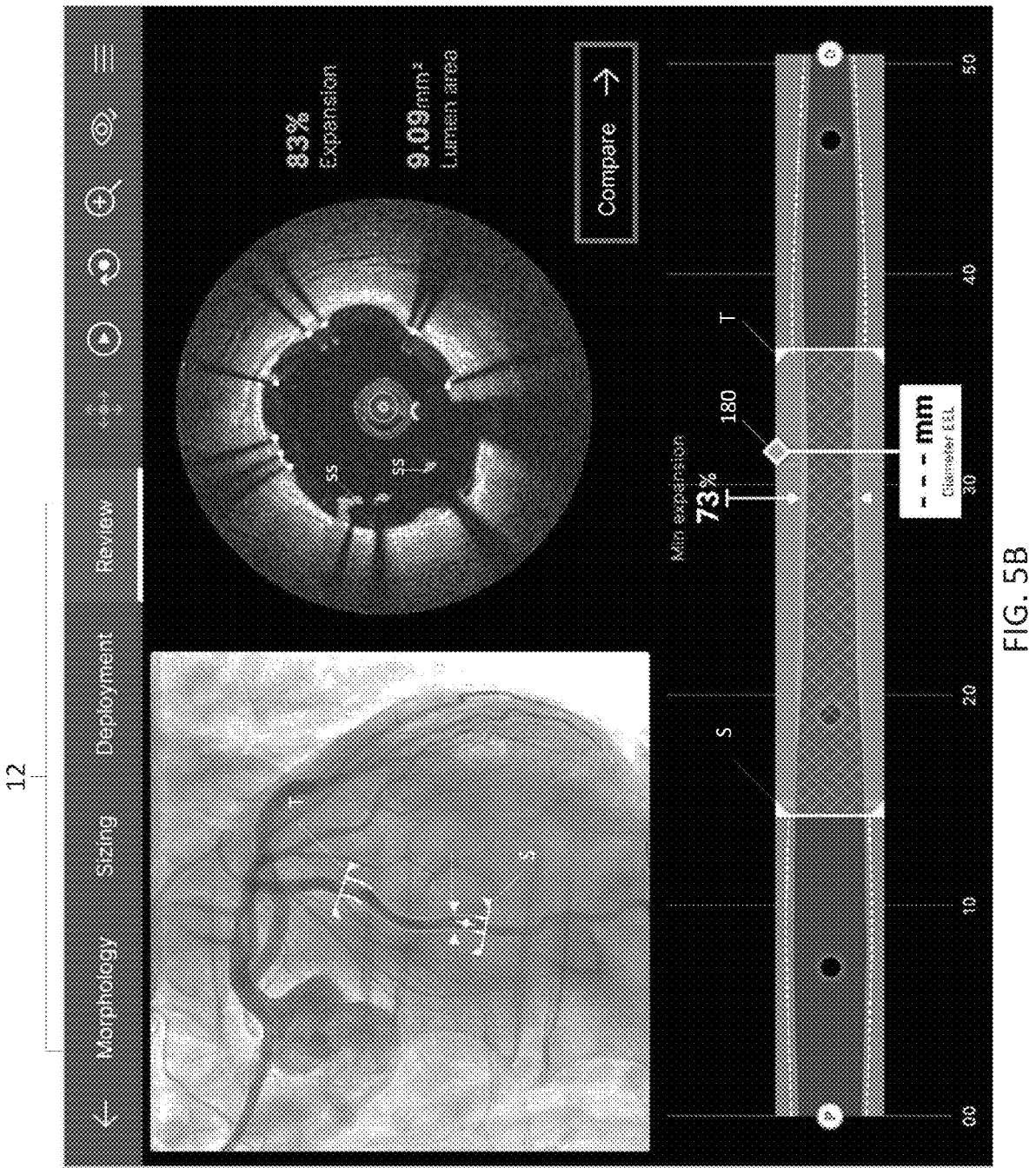
Figure 5C:
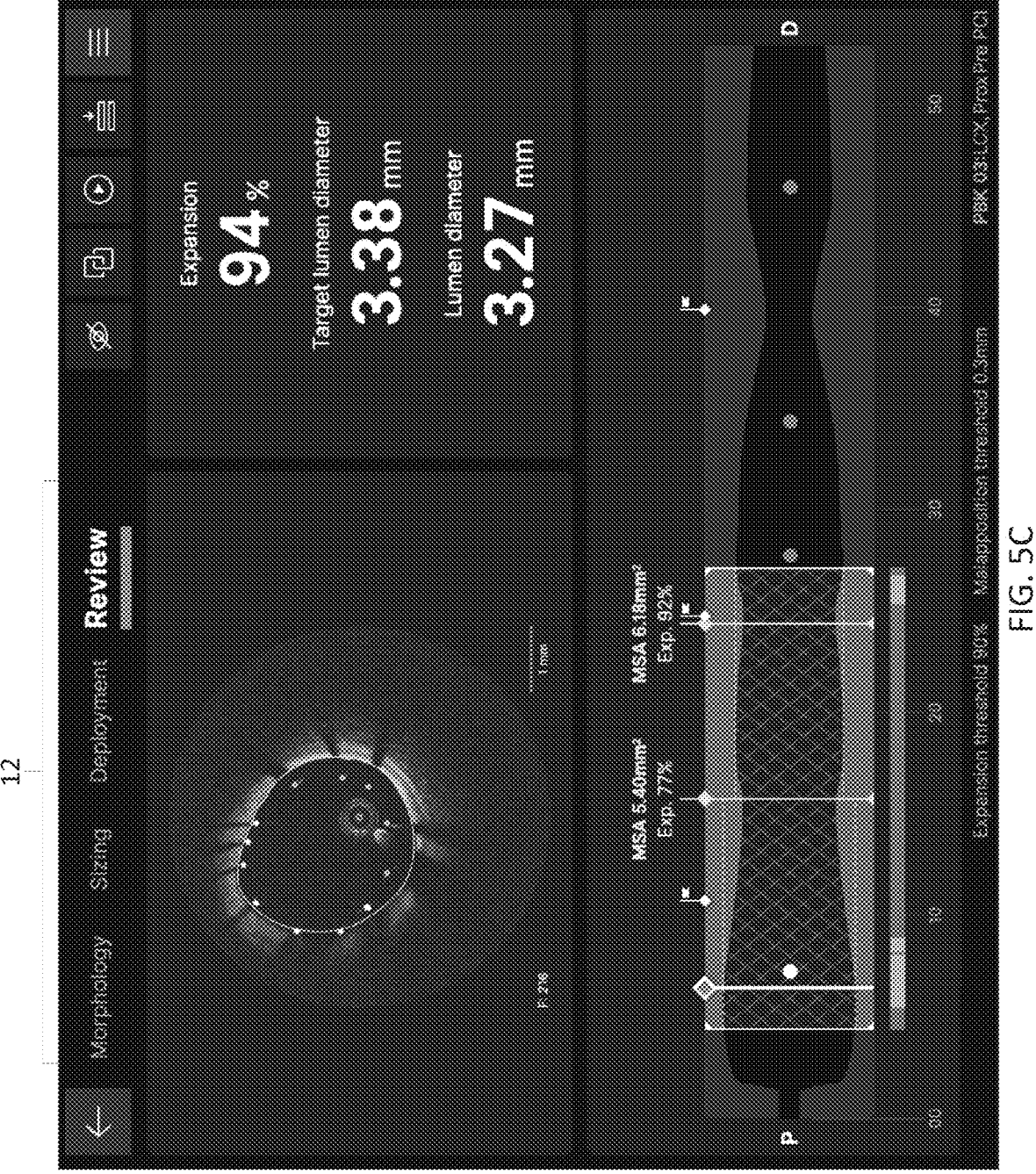
Figure 5D:
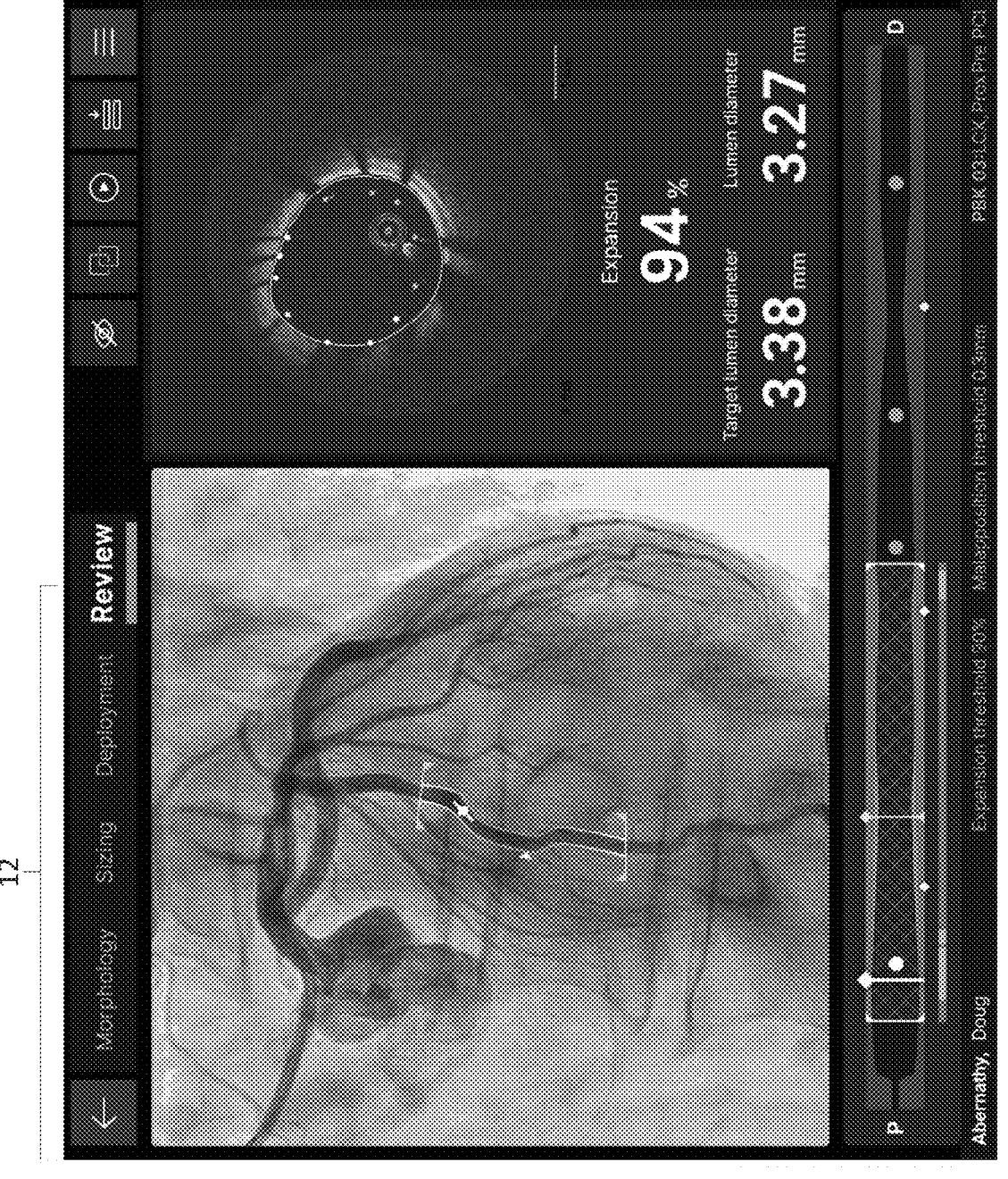

FIG. 5B is a user interface showing a review mode of stent placement relative to an artery representation. In one embodiment, a representation or indicia of a stent is drawn or otherwise depicted or overlaid relative to an image, a representation, In one embodiment, a stent is visualized as a mesh or graphic object with cross-hatching. The landing zones for the stent, S and T, are shown in various views. The EEL diameter is shown at a frame or segment location 180. The minimum stent expansion 73% is shown. The horizontal line shown in color corresponds to stent expansion. Stent expansion for frame or location 180 is also shown in top right with another view showing 83% stent expansion at the point along the stent and a lumen area of about 9.09 at that location/frame 180. Various stent struts SS are also shown in top right view. The color coded length on the right as shown in the angiography correspond to the stent expansion metrics shown below and the malposed frames are identified by color coded vertical lines.

Figure 6:
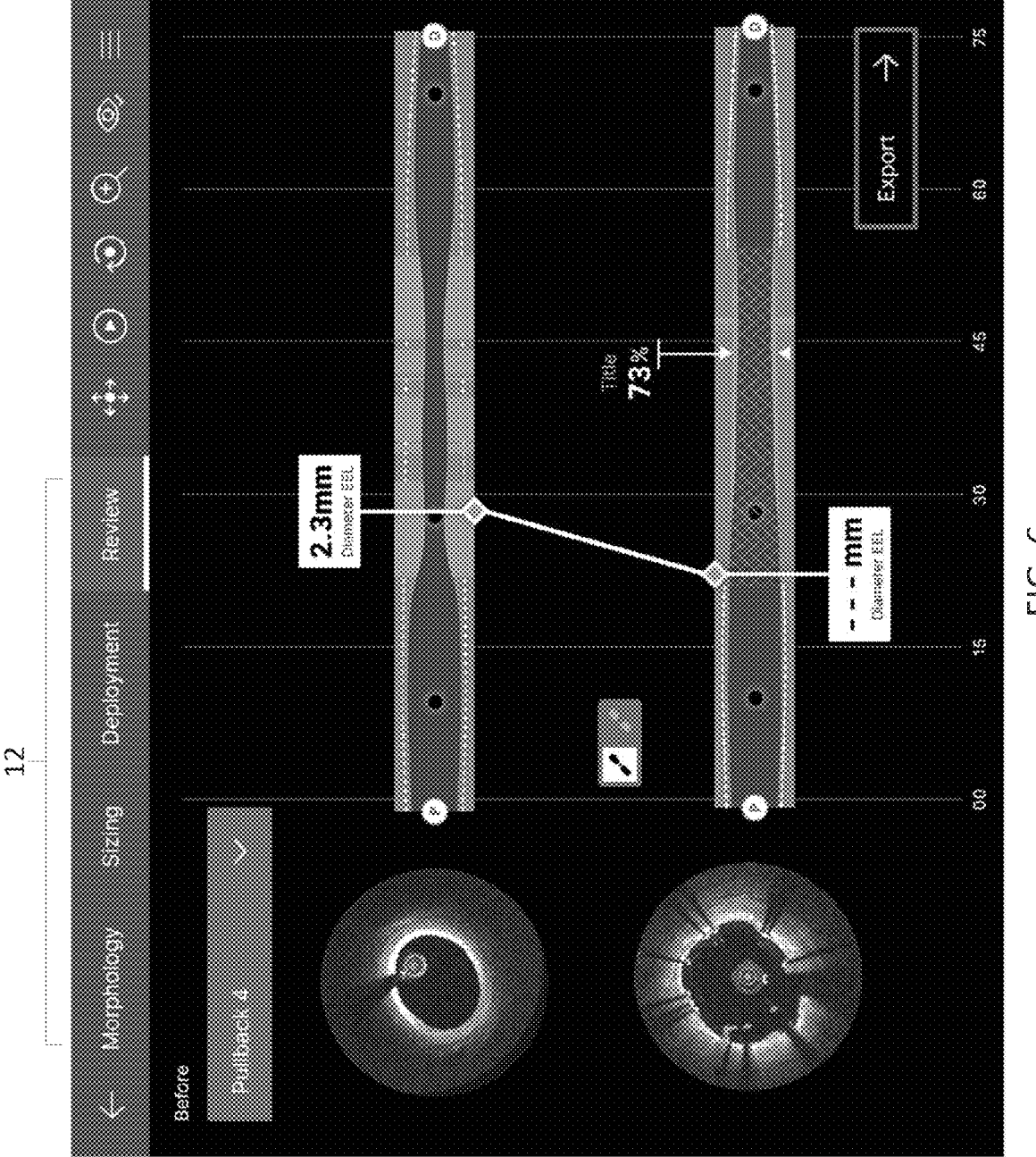

In one embodiment, thin horizontal orange line indicates a difference between target expansion and what is actual is achieve. In one embodiment, orange or another color indicia is used to indicate an under expansion or expansion relative to an expansion threshold or metric. Orange vertical lines or other color coded lines or indicia represent frames with stent malapposition relative to a threshold. In one embodiment, vertical bars are frames with malapposition other indicia such as a color. Examples of this type of representation which can be used in a given user interface are depicted in FIGS. 5A, 5B, 6 (bottom longitudinal view), and FIGS. and 7B. FIG. 5A also shows a malapposition threshold of about 300 um, which is used to display vertical lines corresponding to instances of detected stent struts that are malposed. Various stent struts ST are shown that do not suffer from an underinflated placement or malapposition. Stent struts shown with UM that are disposed in lumen L away from lumen boundary are malposed and/or indicate an underinflated region and are candidates for re-balloon prior to the patient leaving cath lab. The ability to inspect and correct a stent deployment is an important feature of the review workflow.

In one embodiment, a given indicia, such as a color is displayed relative to the user interface to indicate that a parameter associated with a feature or value corresponding to a particular frame, location, region, segment, etc. is above, below or substantially the same as threshold value or level for the value. Thresholds can also be set as greater than or equal to a value/level or less than or equal to a value/level. Thus, detection of calcium, malapposition, stent under expansion, stent over expansion, EEL diameter, EEL radius, other EEL-based parameters, alone or in combination with other parameters, values, levels, etc. disclosed herein or in the figures can be shown using various indicia such as color code regions, vertical lines for one or more frames, horizontal lines hatching, and other indicia. The various indicia can be used as part of a morphology stage, stent sizing stage, stent deployment stage, or a review stage. A given stage corresponds to a workflow in various embodiments.

Figures 7A, 7B:
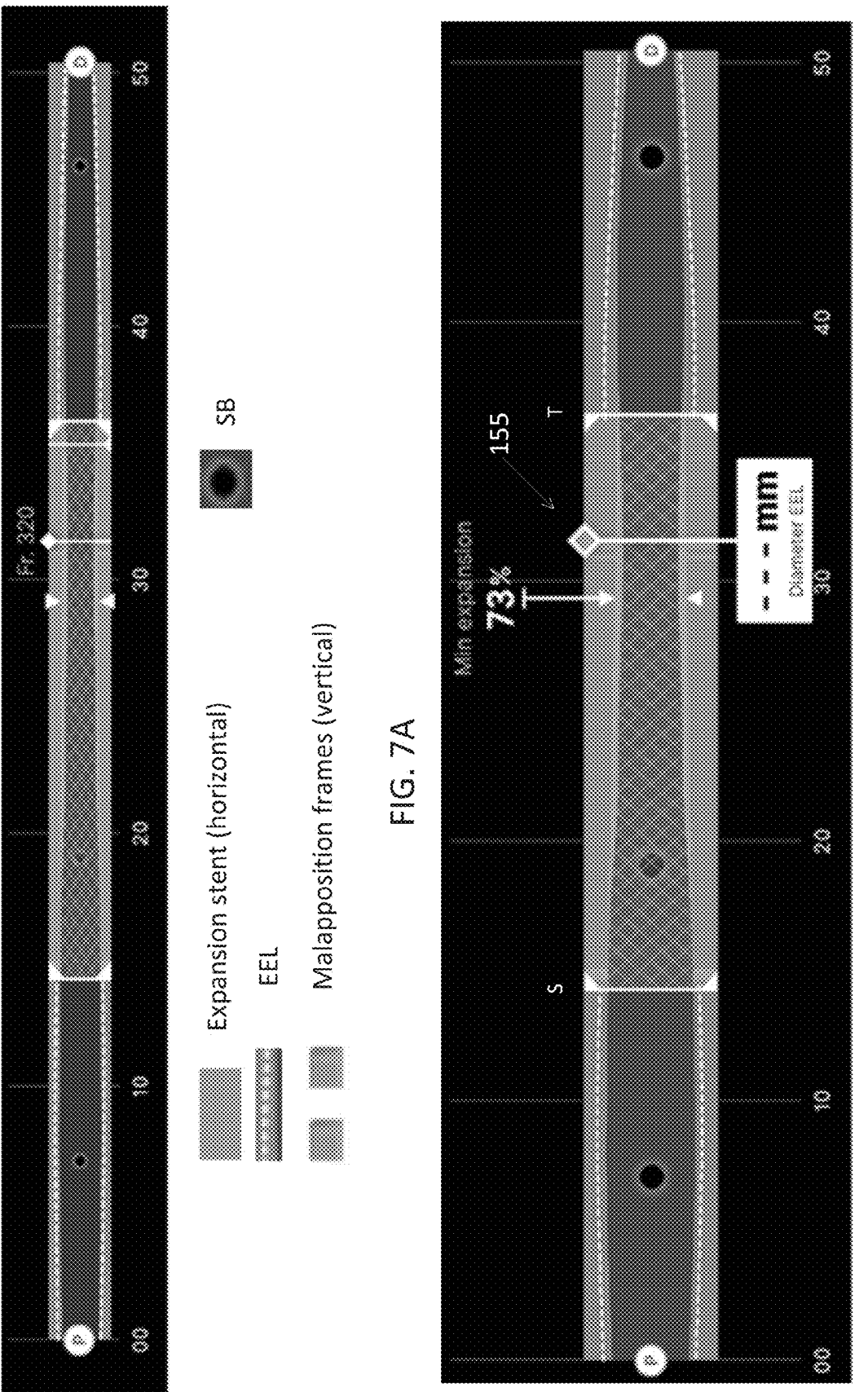

In FIGS. 5A, 7A and 7B, the vertical colored lines or bars are indicative of frame of image data that corresponds to a detected stent strut or stent section that is malposed relative to predetermined or used specified threshold. In addition, the horizontal colored lines or bars or expansion are indicative of frame of image data that corresponds to a detected stent strut or stent section that is under or over expanded relative to predetermined or used specified expansion threshold. Different indicia, such as different colors may be used for stent under expansion or over expansion. In FIG. 6, the top lumen view shows colored regions corresponding to calcium, while in the lower lumen view from a subsequent pullback, the colored regions provided information relating to the deploy stent in terms of malapposition and stent expansion. Various indicia can be combined and/or standardized across differing views with different colors and indicia being used to simplify the interface.

In addition, a given subject may undergo multiple imaging session over the course of a single session with a diagnostician/clinician or over the course of multiple visits in which one or more diagnostic procedures are performed. For example, an intravascular imaging session, such as with OCT imaging can be performed to obtain a morphological assessment showing combined EEL and calcium detections and thresholds as shown in FIGS. 2A and 2B. After that initial session, or first pullback, a stent may be placed and then a subsequent imaging session, such as a second pullback can be performed. These two different sessions typically result in different lengths or segments of the artery being imaged during each session. As a result, although one session or pullback may include imaging data prior to a procedure such as stenting, the subsequent session or pullback includes image data after the stent has been deployed and expanded. Effectively, different length of the same artery can be obtained at different times.

Figure 8:
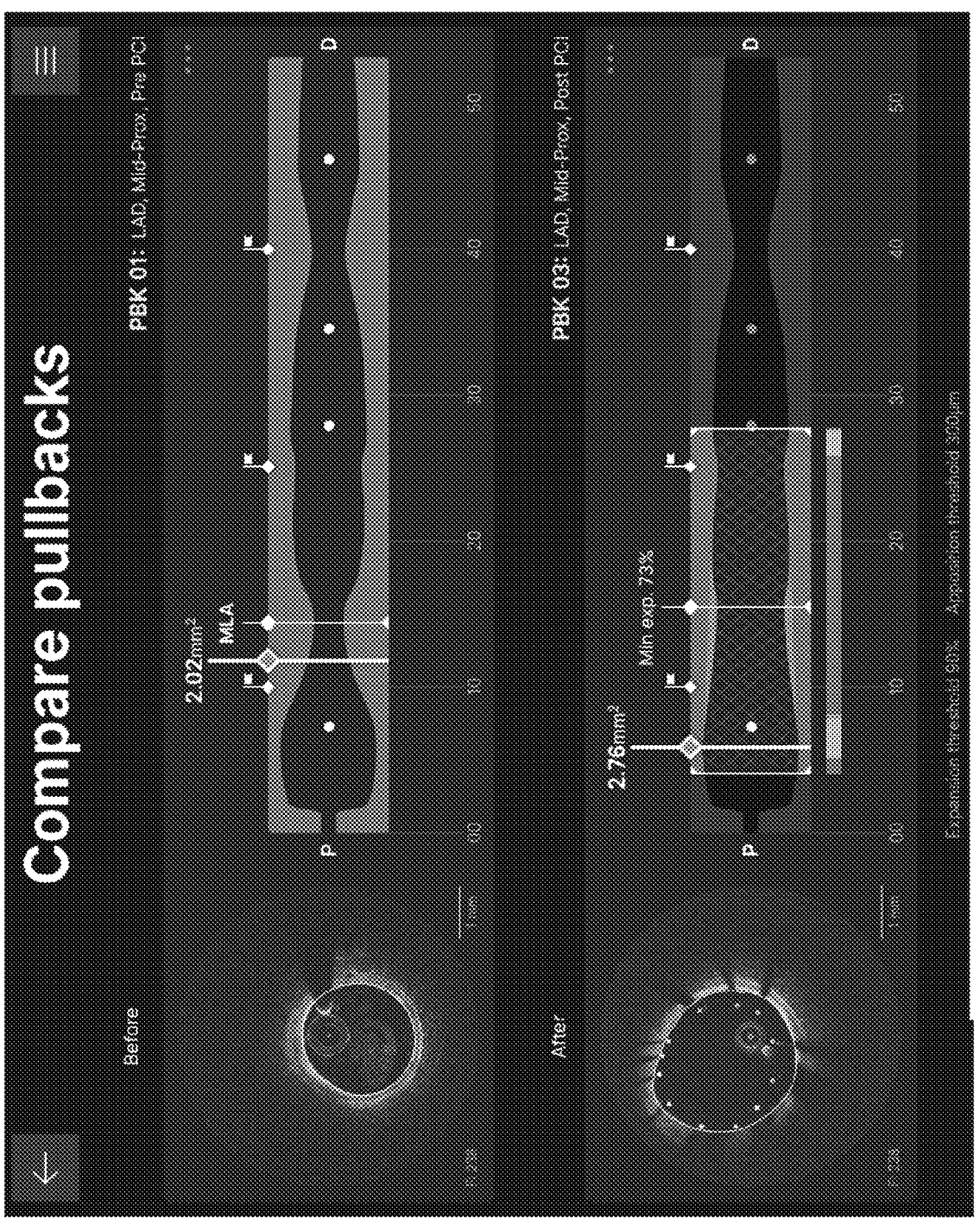

FIG. 8 shows an additional review workflow interface by which as second pullback is compared. The first pullback is shown as before in the upper portion of the interface and the stent shown as being deployed using the other workflows appears in the bottom longitudinal view. The minimum stent expansion amount is shown. A marker for MLA is also shown. The two corresponding cross-sectional frames are also shown on the left where the stent struts within the lumen boundary are also shown. The two measured lumen areas of 2.02 mm2 and 2.76 mm2 (before and after stenting) are also shown. This workflow supports additional balloon before a patient leaves cath lab.

In one embodiment, the user interface, powered by software of underlying diagnostic system, can link the two different set of imaging data, such as first and second pullbacks. In this way, the two sets of data can be synchronized so that they can be scrolled through and common areas of the artery can be reviewed. This facilitates a review of the artery prior to stenting, ballooning, atherectomy, etc. and allows the end user to see the outcome from placing a stent, balloon, or performing an atherectomy. If the two sets of data, first and second pullbacks, were not synchronized, the review would be difficult and tracking location in the artery from two pullbacks with slightly shifted or different contents (frames of image data) would be difficult and possible source of error. This can be seen in FIG. 6. In one embodiment, it is possible for a user to drag the frames to align cross sectional images such that once link scrolling between the two images such as two pullbacks will remain linked/ synchronized.

Lumen detection may be implemented using various systems and methods including those disclosed in U.S. Pat. No. 9,138,147 entitled "Lumen morphology image reconstruction based on the scan line data of OCT," filed on Sep. 22, 2010, the disclosures of which are incorporated by reference in their entirety. In addition, various other detection operations may be implemented using various systems and methods including those disclosed in co-pending application Ser. No. 16/741,718, entitled "SYSTEMS AND METHODS FOR CLASSIFICATION OF ARTERIAL IMAGE REGIONS AND FEATURES THEREOF", filed on Jan. 13, 2020, the disclosures of which are incorporated by reference in their entirety. Further, various other detection operations and details relating to stent analysis and target lumen profiles may be implemented using various systems and methods including those disclosed in co-pending application Ser. No. 14/115,527, entitled "METHOD AND APPARATUS FOR AUTOMATED DETERMINATION OF A LUMEN CONTOUR OF A STENTED BLOOD VESSEL". filed on Mar. 12, 2013, the disclosures of which are incorporated by reference in their entirety.

In part, one embodiment of the disclosure relates to an intravascular data collection system and one or more software-based graphic user interfaces and software modules to perform one or more detection and display processes as described herein. In one embodiment, intravascular data is collected while angiography data is simultaneously collected.

In part, the disclosure relates systems and methods for treatment assessment including stent planning and surgical options by visualizing a subject's blood vessels such as one or more coronary arteries. The image data can be obtained using an intravascular data collection probe. The probe can be pulled back through a blood vessel and data can be collected with respect thereto. Such pullbacks and the associated data collection are used to plan stent deployment or evaluate deployed stents. The resulting intravascular data from a pullback can be used in various ways such as to visualize various blood vessel regions, features, and stents deployed in relation thereto. The image data, artery representations (cross-sectional, longitudinal, and other views of imaged artery), and detections shown relative to the artery representations can be co-registered with corresponding angiography data. Thus, a user can select a region of a an artery representation as part of a workflow and see the underlying image data used to generate the map (OCT, IVUS, x-ray, etc.) and also see the angiography data with highlighting or other indicia showing the region of the blood vessel that was selected on the artery representation or view. This can be implemented using a co-registration workflow.

In part, the disclosure relates to intravascular data collection systems, such as OCT, IVUS, and other imaging modalities and the generation and visualization of diagnostic information such as stent landing zones, side branches, regions of interest, and characterized tissue regions in the blood vessel and shown as a sequence of workflows that are computer guided based on various user interface layout and sequence of operations as part of a given imaging and diagnostic session in the cath lab. Graphical elements suitable for indicating diagnostic information of interest such as the foregoing serve as user selected elements that allow for comparison, measurement, and analysis. Notwithstanding this point, various detections and workflow related display are generated automatically to help reduce end user information overall load and associated fatigue by succinctly organizing and summarizing the relevant information.

Also disclosed herein are systems and methods for visualizing stents, tissue types, tissue volumes, and tissue boundaries. The systems and methods disclosed herein also include automated measurement systems and related features that can measure angles, thickness, volume, width, frame count, relative proximity of tissue to lumen, of various tissue types including calcium, lipid, fiber and others. In various embodiments, such measurement tools can be used be used to measure the foregoing parameters such as Ca, EEL, and lumen thickness and any geometric property for a given region of interest for a particular tissue type. These measurements can be used to generate various ratings or scores suitable for consideration by end users.

An intravascular image or frame, such as the cross-sectional images of the figures are typically acquired one scan line at a time. A sequence of samples along a ray originating at the catheter center to the maximum imaging depth is referred to as a scan line in one embodiment. In one embodiment, the smallest data unit in an OCT image is called a sample. A sequence of samples along a ray originating at the probe center to the maximum imaging depth is called a scan line. An OCT image is typically acquired one scan line at a time. A cross-sectional image can be formed from a set of scan lines collected as the probe rotates. Further, to image a segment of an artery or other vessel, the catheter is moved longitudinally while rotating. In this way, the probe acquires a set of cross-sectional images in a spiral pattern. The images originate from the various scan lines associated with a slice of the vessel or artery of interest. The scan lines are arranged with angles between them like spokes on a wheel. Scan lines are acquired in a polar format in one embodiment.

It will be appreciated that for clarity, the disclosure explicates various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The detailed description of embodiments is not to be regarded as limiting the scope of the applicant's teachings in any manner.

The terms "about" and "substantially identical" as used herein, refer to variations in a numerical quantity that can occur, for example, through measuring or handling procedures in the real world; through inadvertent error in these procedures; through differences/faults in the manufacture of electrical elements; through electrical losses; as well as variations that would be recognized by one skilled in the art as being equivalent so long as such variations do not encompass known values practiced by the prior art. Typically, the term "about" means greater or lesser than the value or range of values stated by 1/10 of the stated value, e.g., ±10%. For instance, applying a voltage of about +3V DC to an element can mean a voltage between +2.7V DC and +3.3V DC. Likewise, wherein values are said to be "substantially identical," the values may differ by up to 5%. Whether or not modified by the term "about" or "substantially" identical, quantitative values recited in the claims include equivalents to the recited values, e.g., variations in the numerical quantity of such values that can occur, but would be recognized to be equivalents by a person skilled in the art.

Non-Limiting Software Features and Embodiments for Arterial Assessment Using Intravascular and Other Imaging Modalities, Workflow Presentation and Sequencing and Graphical User Interface Features, Systems and Methods The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like. The disclosure can also be practiced in distributed computing environments where tasks are performed by remote processing devices that are linked through a communications network such as in different rooms of a catheter or cath lab.

In one embodiment, software modules designed to operate upon intravascular data to characterize the tissue and identify regions of interest such as calcium regions, taper regions, lipid pools, and other tissue features such as. The software can also compare Fractional Flow Reserve (FFR), Vascular Resistance Ratio (VRR), and other measured and calculated intravascular data collection parameters. To the extent such parameters change from a stented state to a non-stent state, such parameters can be used to generate one or more metrics.

In one embodiment, an OCT system can be used. The system includes an optical receiver such as a balanced photodiode based system receives light returned by the probe. A computing device, such as a computer, a processor, an ASIC or other device that is part of the system or is included as a separate subsystem in electrical or optical communication with the system and receives electronic signals from the probe. The computing device in various embodiments includes local memory, buses and other components suitable for processing data and utilizing software such as image data processing configured for stent visualization and stent malapposition detection. In one embodiment, a PCIe bus or other high-band width, low latency bus is used to connect various components of a given imaging system, MLS, or combination system that includes both.

Figure 3B:
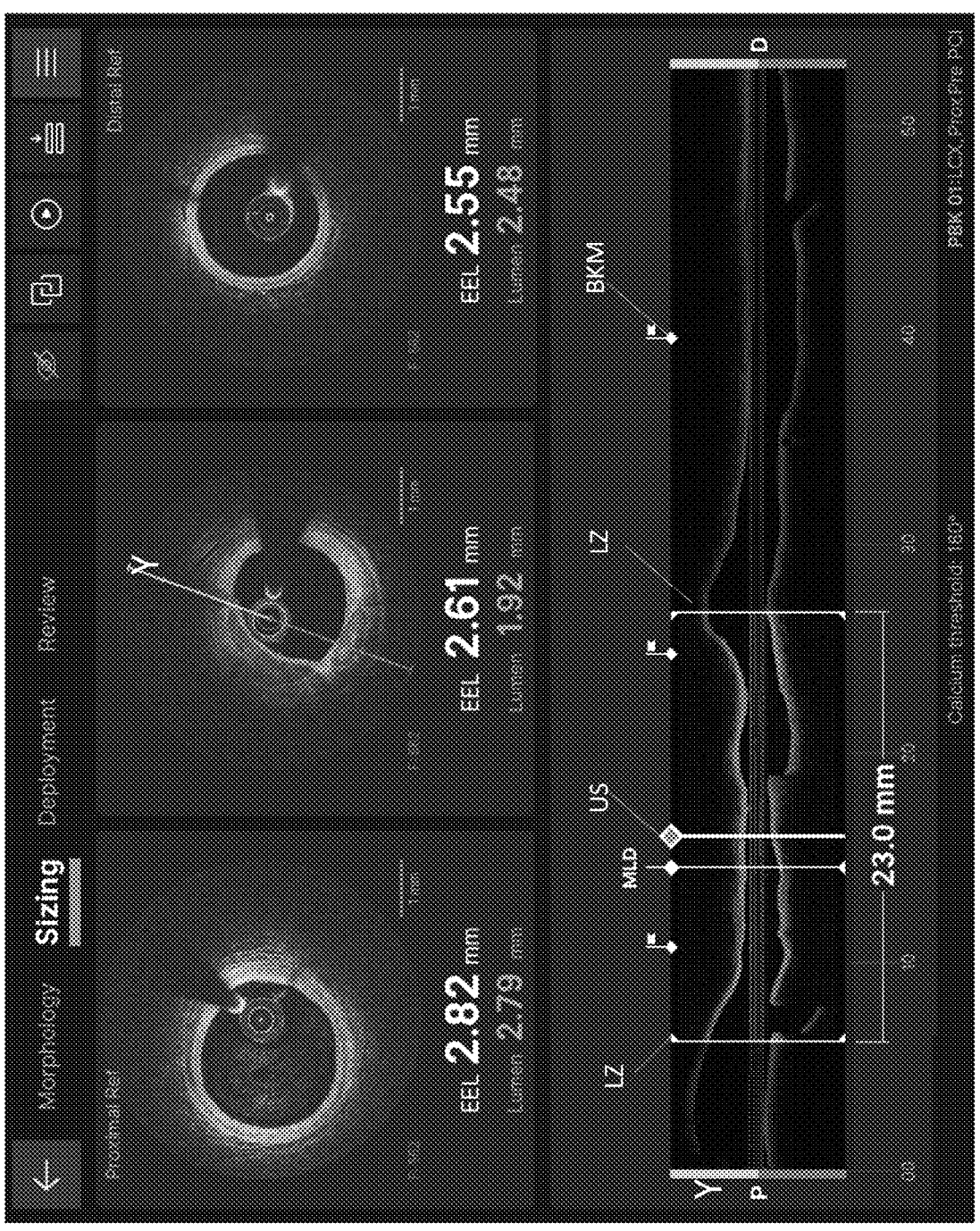
Figure 3C:
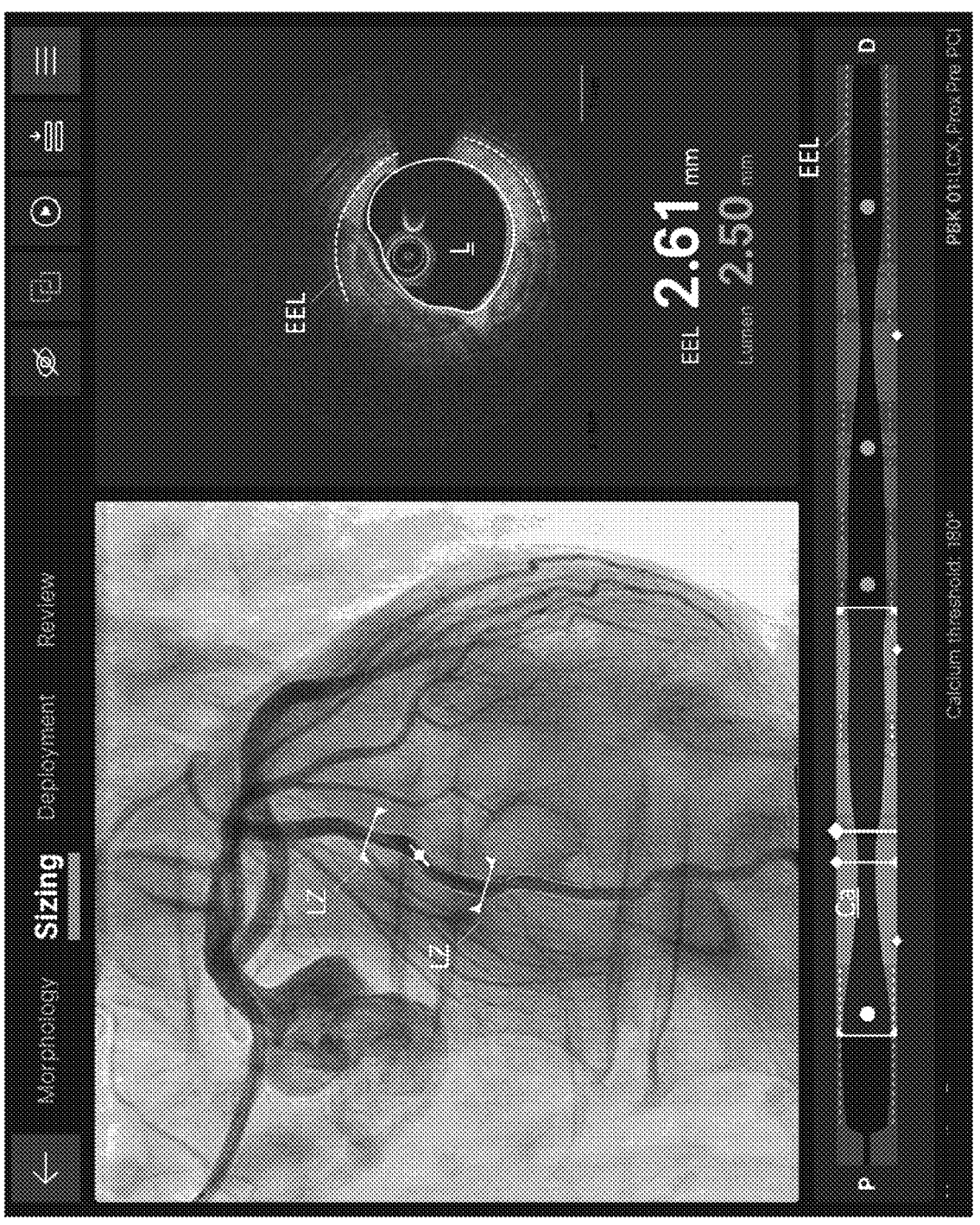
Figure 3D:
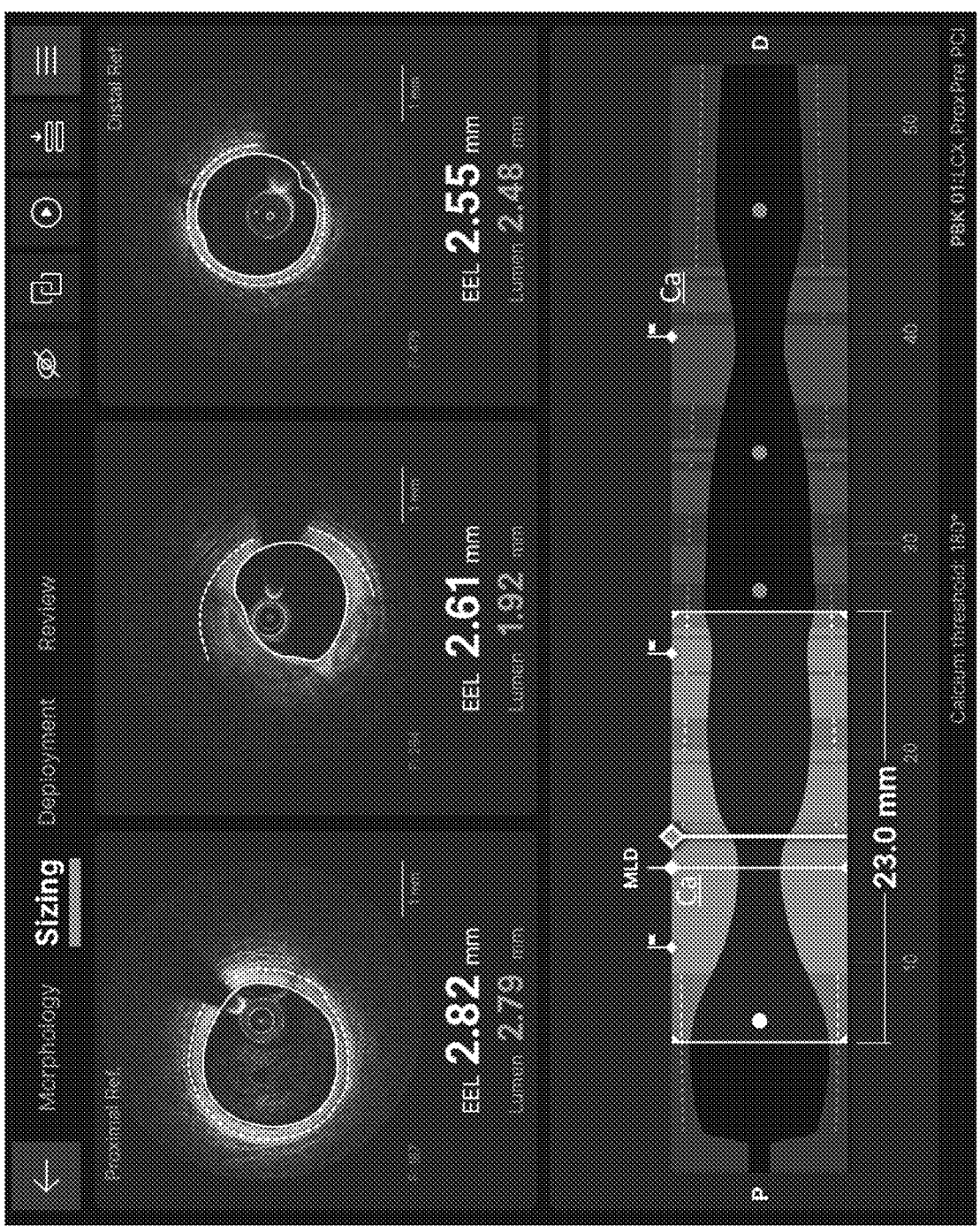

The stent deployment planning tools can be part of or exchange data with software. These tools can be used to place a virtual stent in the lumen area that the probe is disposed in relative to vessel wall. FIG. 3B sand 3C shows an exemplary region of a segment of a pullback wherein one or more virtual stents can be deployed and displayed on a user interface. In FIG. 3C, the candidate stent landing zones LZ during sizing workflow are shown co-registered relative to an angiography image. A cross-sectional representation of a frame of artery is also shown with an EEL diameter of 2.61 mm and a lumen diameter of 2.50 mm. These measurements can be used to help inform stent selection and co-registration with angio helps landing zones be evaluated and changed. The top portion of the distal reference and proximal reference frame is yellow and the bottom portion is blue in FIG. 3B. In FIG. 3B, as part of the sizing candidate landing zones LZ and a candidate stent length 23 mm has been selected by a user. Three frames are shown with user selectable frame in the middle. In various embodiments, marker US can be moved to change which frame is displayed in middle panel of stent sizing graphical interface to allow different EEL and lumen diameters to be considered relative to proximal and distal references. A bookmark BKM is also shown that can be set by a user using GUI so they can move between frames quickly. Another marker showing the frame with the minimum lumen diameter MLD is shown, in other instances the MLA, or minimum lumen area can be displayed.

A display can also be part of the system for showing information such as cross-sectional and longitudinal views of a blood vessel generated using collected intravascular data. Once the intravascular data is obtained with the probe and stored in memory, it can be processed to generate and display information such as a cross-sectional, a longitudinal, and/or a three-dimensional view of the blood vessel along the length of the pullback region or a subset thereof. Two or three dimensional image masks can be used to show or store ground truth data and predictive outcomes. These views can be depicted as part of a user interface as shown and described below and in subsequent figures.

A given set of user interfaces can be organized pursuant to the workflows as disclosed herein. In various embodiments, the workflows have a preferred order that operates to streamline operations in the cath lab and improve patient outcomes prior to the patient being discharged, or in fact, leaving the cath lab table. In one embodiment, the sequence of workflows is performed in the following sequence: morphology, stent sizing, stent deployment, and review. The images of the blood vessel generated using the distances measurements obtained from the system provide information about the blood vessel including lumen contours, vessel diameters, vessel cross-sectional areas, landing zones, and a virtual stent bounded by the landing zones when processed using the tools and software modules described herein. In one embodiment, the MLS includes one or more computing devices and one or more software programs or modules. There various devices, components, systems, and subsystems disclosed herein are operable to perform the tasks, methods, steps, processes and other features described herein relative to each of the foregoing.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "classifying" or "characterizing" or "correlating" or "detecting" "assessing" or "convolving" or "de-convolving" or "classifying" or "segmenting" or "training" or "annotating" or "registering" or "measuring" or "calculating" or "comparing" "generating" or "sensing" or "determining" or "displaying," or Boolean logic or other set related operations or the like, refer to the action and processes of a trained MLS, computer system, AI processor, GPU, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages.

In one embodiment, semantic segmentation using a given MLS embodiment can be used to detect if image has calcium and EEL and identify the pixels with calcium and EEL. This helps physicians solve various problems relating to selecting treatment options and guiding a particular treatment. In various embodiments, the outputs of the MLS system include one or more of arc-based metrics/measurements of similarity for both Ca and EEL; detected EEL diameters; and detected Ca depth. In some embodiments, these values are measured relative to image data after classifying EEL, media, calcium, lumen, and other regions and features of interest. Some non-limiting examples of tissue types for which the methods and systems disclosed herein can be used to detect include inner region where blood flows, the lumen, the intima, the media, external elastic lamina (EEL) (also referred to as external elastic membrane), internal elastic lamina (IEL), adventitia, plaque, calcium or calcified tissue, and others. The media is bounded by the IEL and EEL. The intima is bounded by the lumen and the IEL. The disclosure relates to various embodiments that use one or more machine learning or artificial intelligence (AI) systems to detect or segment an image of an artery or other structure into various component tissue types or regions of interest. In part, the machine learning systems are designed such that they can be installed or combined with an imaging system such as an intravascular imaging system, an ultrasound system, or an x-ray system such as an angiography or fluoroscopy system. In one embodiment, the disclosure relates to using an MLS to perform tissue characterization to detect one or more of Lumen, EEL, Media, and calcium/calcium plaques.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using an intravascular imaging system that may include one or more imaging probes for pullbacks, 2D imaging, or 3D imaging system, and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating training sets, image masks, and other inputs and outputs disclosed herein. Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Python, Perl, Go, FORTRAN, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

Various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET, SQL, or MySQL, using, for example, conventional or object-oriented techniques.

Programming languages for computer software and other computer-implemented instructions may be translated into machine language by a compiler or an assembler before execution and/or may be translated directly at run time by an interpreter. Examples of assembly languages include ARM, MIPS, and x86; examples of high level languages include Ada, BASIC, C, C++, C #, COBOL, Fortran, LUA, Clojure, Java, Lisp, Pascal, Object Pascal; and examples of scripting languages include Bourne script, JavaScript, Python, Ruby, PHP, and Perl.

The operation and behavior of the embodiments are described without specific reference to the actual software code or specialized hardware components. The absence of such specific references is feasible because it is clearly understood that artisans of ordinary skill would be able to design software and control hardware to implement the embodiments of the present disclosure, based on the description herein with only a reasonable effort and without undue experimentation.

The various machine learning systems and associated neural networks such as deep learning neural networks, 3D neural networks, convolutional neural networks, 2D neural networks, N layer neural networks, feed forward neural networks, feed forward network, feed backward network, radial basis function neural network, Korhonen self-organizing neural network, recurrent neural network (RNN), modular neural network, deep learning network, artificial intelligence-based systems and frameworks, and combinations of the foregoing.

The software for the various diagnostic systems described herein, which may be implementing using combinations of controllers, processors, computing devices, ASICS, FPGAs, and/or combinations thereof and other computer functions described herein may be implemented in computer software using any suitable computer programming language. For example, the various machine learning systems may be implemented with software modules stored or otherwise maintained in computer readable media, e.g., RAM, ROM, secondary storage, etc. One or more processing cores (e.g., CPU, GPU and/or AI accelerator cores) may generate sequence of workflows and graphic user interfaces and respond to user actions, such as joystick, button, mouse, and other user interface devices.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed herein. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as resistance changes, voltage changes, current changes, guidewire-based probe data, intravascular pressure data, ratios, calcium thickness, EEL thickness, calcium angle, indices and other information of interest as disclosed herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

In part, the disclosure relates to diagnostic systems and interfaces for the same that facilitate navigating a blood vessel representation with respect to which one or more imaging and tissue detection methodologies has been applied. With respect to a given blood vessel, such as a coronary artery or other body lumen, one or more tissue types or other regions of interest can be identified using various techniques. In particular, calcium nodules, calcified tissue and other calcium associated tissues can be represented such as calcified regions in blood vessels. One or more artery representations can be generated and used to displaying characterized tissue and regions of interest to a user as part of a given system directed workflow.

The characterized tissues and/or regions of interest suitable for detection and inclusion on a one or more graphical user interfaces, which can be displayed simultaneous to include proximal segments, distal segments, and user selected segments or frames to streamline the information use when selecting or deploying a stent. These graphical user interfaces may display features that have been automatically detected and displayed to user with one or more visualizable element or indicia such as color, hatching, animation, etc. Suitable features for automatic detection and display with one or more indicia can include one or more of the following lipid regions, lumen regions, stent struts, side branches, guidewires, external elastic layer (EEL), internal elastic layer (IEL), boundaries and volumes relating to the forgoing and other arterial features and tissues types as disclosed herein. Various axes can be color code, in part, or modified with an indicia such that an axis in one view, such as a cross-sectional view tracks with the same axis in a longitudinal view. This is show with blue and yellow color code line segment/axis portions in FIGS. 2D and 3B for example.

In part, the disclosure relates to intravascular data collection systems, such as OCT, IVUS, and other imaging modalities and the generation and visualization of diagnostic information such as stent landing zones, side branches, regions of interest, and characterized tissue regions in the blood vessel. Graphical elements suitable for indicating diagnostic information of interest such as the foregoing serve as user selected elements in the workflows such as markers.

Also disclosed herein are systems and methods for visualizing stents, tissue types, tissue volumes, and tissue boundaries. One or more software modules can be used to detect side branch locations, lumen contours, and stent strut positions, generate a blood vessel representation, and control navigation to images based on user selections relative to a GUI. The systems and methods disclosed herein also include automated measurement systems and related features that can measure angles, arcs, circumferential portions, thickness, volume, width, frame count, relative proximity of tissue to lumen, of various tissue types including calcium, lipid, fiber and others.

In various embodiments, such measurement tools can be used be used to measure the foregoing parameters and any geometric property for a given region of interest for a particular tissue type. These measurements can be used to generate various ratings or scores suitable for consideration by end users. For example, if calcium burden in a particular region of a vessel appears but overall is only a minor amount of surface calcium, measurements relative thereto can help guide a user and not exclude such a region as a candidate landing zone.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph. Absent a recital of "means for" in the claims, such claims should not be construed under 35 USC 112. Limitations from the specification are not intended to be read into any claims, unless such limitations are expressly included in the claims.

When values or ranges of values are given, each value and the end points of a given range and the values there between may be increased or decreased by 20%, while still staying within the teachings of the disclosure, unless some different range is specifically mentioned.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A method, comprising:
   receiving, by one or more processors, extraluminal image data and intravascular data of a vessel, the intravascular data comprising intravascular image frames;
   generating, by the one or more processors based on the intravascular data, a two-dimensional representation of the vessel, wherein the two-dimensional representation is symmetrical relative to a longest axis of the two-dimensional representation;

determining, by the one or more processors based on the intravascular data, external elastic lamina (EEL) of the intravascular image frames; and providing for output, by the one or more processors, the extraluminal image data, at least one of the intravascular image frames including a curved indicator corresponding to the EEL, and the two-dimensional representation including a first indication corresponding to the EEL.

2. The method of claim 1, wherein the feature of interest is at least one of calcium or lipid.

3. The method of claim 2, wherein the arc extends at least partially around a perimeter of the at least one of the intravascular image frames.

4. The method of claim 2, further comprising:

automatically detecting, by the one or more processors based on the intravascular data, one or more regions of calcium relative to a lumen boundary of the vessel on a per intravascular image frame basis; and determining, by the one or more processors for one or more intravascular image frames, an angular or circumferential measurement of detected calcium.

5. The method of claim 4, further comprising determining, by the one or more processors for the one or more intravascular image frames, a calcium thickness of detected calcium.

6. The method of claim 1, wherein the curved indicator is output as an overlay on the at least one of the intravascular image frames.

7. The method of claim 1, further comprising determining, by the one or more processors based on the intravascular data, a feature of interest, wherein:

the at least one of the intravascular image frames further includes an arc corresponding to the feature of interest, and the two-dimensional representation further includes a second indication corresponding to the feature of interest.

8. The method of claim 1, further comprising:

receiving an input in connection with the two-dimensional representation corresponding to a selection of an intravascular image frame; and updating, by the one or more processors, the output of the at least one of the intravascular image frames to correspond to the selected intravascular image frame.

9. The method of claim 1, further comprising:

co-registering, by the one or more processors, one or more candidate stent landing zones to the extraluminal image data; and providing for output, by the one or more processors, at least one landing zone indication on the extraluminal image data.

10. The method of claim 9, further comprising providing for output, by the one or more processors, the at least one landing zone indication on the two-dimensional representation.

11. The method of claim 1, further comprising co-registering, by the one or more processors, the EEL with the two-dimensional representation of the vessel and the intravascular image frames.

12. A system, comprising:

one or more processors, the one or more processors configured to:

receive extraluminal image data and intravascular data of a vessel, the intravascular data comprising intravascular image frames;

generate, based on the intravascular data, a two-dimensional representation of the vessel, wherein the two-dimensional representation is symmetrical relative to a longest axis of the two-dimensional representation;

determine, based on the intravascular data, external elastic lamina (EEL) of the intravascular image frames; and provide for output the extraluminal image data, at least one of the intravascular image frames including a curved indicator corresponding to the EEL, and the two-dimensional representation including a first indication corresponding the EEL.

13. The system of claim 12, wherein the curved indicator is output as an overlay on the at least one of the intravascular image frames.

14. The system of claim 12, wherein:

the one or more processors are further configured to determine, based on the intravascular data, a feature of interest, the at least one of the intravascular image frames further includes an arc corresponding to the feature of interest, and the two-dimensional representation further includes a second indication corresponding to the feature of interest.

15. The system of claim 14, wherein the feature of interest is at least one of calcium or lipid.

16. The system of claim 15, wherein the arc extends at least partially around a perimeter of the at least one of the intravascular image frames.

17. The system of claim 15, wherein the one or more processors are further configured to:

automatically detect, based on the intravascular data, one or more regions of calcium relative to a lumen boundary of the vessel on a per intravascular image frame basis; and determine, for one or more intravascular image frames, an angular or circumferential measurement of detected calcium.

18. The system of claim 12, wherein the one or more processors are further configured to:

co-register one or more candidate stent landing zones to the extraluminal image data; and provide for output at least one landing zone indication on at least one of the extraluminal image data or the two-dimensional representation.

19. One or more non-transitory computer-readable medium storing instructions which, when executed by one or more processors, cause the one or more processors to:

receive extraluminal image data and intravascular data of a vessel, the intravascular data comprising intravascular image frames;

generate, based on the intravascular data, a two-dimensional representation of the vessel, wherein the two-dimensional representation is symmetrical relative to a longest axis of the two-dimensional representation;

determine, based on the intravascular data, external elastic lamina (EEL) of the intravascular image frames; and provide for output the extraluminal image data, at least one of the intravascular image frames including a curved indicator corresponding to the EEL, and the two-dimensional representation including a first indication corresponding the EEL.

* * * * *